US012673134B2

(12) United States Patent
Kanesato et al.

(10) Patent No.: US 12,673,134 B2
(45) Date of Patent: Jul. 7, 2026

(54) GELATIN-CONTAINING DEVICE

(71) Applicants: Shin-Etsu Chemical Co., Ltd., Tokyo (JP); JAPAN VAM & POVAL CO., LTD., Osaka (JP); TOHOKU UNIVERSITY, Miyagi (JP); KYOTO MEDICAL PLANNING Co., Ltd., Kyoto (JP)

(72) Inventors: Shuhei Kanesato, Tokyo (JP); Yoshihiro Kimura, Osaka (JP); Akinobu Oharuda, Osaka (JP); Masafumi Goto, Miyagi (JP)

(73) Assignees: SHIN-ETSU CHEMICAL CO., LTD., Tokyo (JP); JAPAN VAM & POVAL CO., LTD., Osaka (JP); TOHOKU UNIVERSITY, Miyagi (JP); KYOTO MEDICAL PLANNING CO., LTD., Kyoto (JP)

( * ) Notice: Subject to any disclaimer, the term of this patent is extended or adjusted under 35 U.S.C. 154(b) by 277 days.

(21) Appl. No.: 18/276,124

(22) PCT Filed: Feb. 8, 2022

(86) PCT No.: PCT/JP2022/004982
§ 371 (c)(1),
(2) Date: Aug. 7, 2023

(87) PCT Pub. No.: WO2022/172929
PCT Pub. Date: Aug. 18, 2022

(65) Prior Publication Data
US 2024/0091404 A1 Mar. 21, 2024

(30) Foreign Application Priority Data

Feb. 9, 2021 (JP) ................................. 2021-019174

(51) Int. Cl.
*A61L 27/22* (2006.01)
*A61L 27/38* (2006.01)
*A61L 27/58* (2006.01)

(52) U.S. Cl.
CPC ............. *A61L 27/222* (2013.01); *A61L 27/38* (2013.01); *A61L 27/58* (2013.01)

(58) Field of Classification Search
CPC ........ A61L 27/222; A61L 27/58; A61L 27/38; C12N 5/0677
See application file for complete search history.

(56) References Cited

U.S. PATENT DOCUMENTS

| | | |
|---|---|---|
| 2004/0063200 A1 | 4/2004 | Chaikof et al. |
| 2004/0110439 A1 | 6/2004 | Chaikof et al. |
| 2012/0253472 A1 | 10/2012 | Priewe |
| 2014/0141050 A1 | 5/2014 | Plöger et al. |
| 2016/0199530 A1 | 7/2016 | Plöger et al. |
| 2016/0228473 A1 | 8/2016 | Iwata et al. |
| 2018/0008743 A1 | 1/2018 | Plöger et al. |
| 2019/0365947 A1 | 12/2019 | Oharuda et al. |
| 2020/0231960 A1 | 7/2020 | Oharuda et al. |
| 2020/0289715 A1 | 9/2020 | Heffels et al. |
| 2020/0289716 A1 | 9/2020 | Heffels et al. |

FOREIGN PATENT DOCUMENTS

| | | |
|---|---|---|
| CN | 103442741 | 12/2013 |
| CN | 105764538 | 7/2016 |
| CN | 107551322 | 1/2018 |
| EP | 0 299 010 | 6/1996 |
| JP | 2002-145797 | 5/2002 |
| JP | 2004-525268 | 8/2004 |
| JP | 2014-522918 | 9/2014 |
| JP | 6450894 | 1/2019 |
| JP | 2021-500178 | 1/2021 |
| WO | 2018/155621 | 8/2018 |
| WO | 2018/155622 | 8/2018 |
| WO | 2018/235745 | 12/2018 |
| WO | 2020/262458 A1 * | 12/2020 |
| WO | WO 2020/262458 * | 12/2020 |

OTHER PUBLICATIONS

Extended European Search Report issued Dec. 6, 2024 in corresponding European Patent Application No. 22752752.0.
Qi et al., "PVA hydrogel sheet macroencapsulation for the bioartificial pancreas", Biomaterials, vol. 25, No. 27 (Dec. 1, 2004), pp. 5885-5892.
Zhu et al., "Biomimetic hybrid scaffold of electrospun silk fibroin and pancreatic decellularized extracellular matrix for islet survival", Journal of Biomaterials Science, Polymer Edition, vol. 32, No. 2 (Sep. 15, 2020), pp. 151-165.
International Preliminary Report on Patentability issued Aug. 15, 2023 in International (PCT) Application No. PCT/JP2022/004982.
International Search Report (ISR) issued Apr. 26, 2022 in International (PCT) Application No. PCT/JP2022/004982.
Office Action issued May 4, 2026 in corresponding European Patent Application No. 22 752 752.0.
Atsushi Azumaguchi et al., "Efficacy of silicone sheet as a personalized barrier for preventing adhesion reformation after hysteroscopic adhesiolysis of intrauterine adhesions", Reproductive Medicine and Biology, vol. 18, No. 4, Sep. 6, 2019, pp. 378-383.
Jiannan Li et al., "Polymer materials for prevention of postoperative adhesion", Acta Biomaterialia, vol. 61, Aug. 2, 2017, pp. 21-40.

* cited by examiner

*Primary Examiner* — Carlos A Azpuru

(74) *Attorney, Agent, or Firm* — Wenderoth, Lind & Ponack, L.L.P.

(57) ABSTRACT

Provided is a novel device (implantation device) containing a gelatin. The implantation device is made of a bioabsorbable non-woven fabric containing a gelatin.

16 Claims, No Drawings

GELATIN-CONTAINING DEVICE

TECHNICAL FIELD

The present invention relates to a novel gelatin-containing device and others.

BACKGROUND ART

Cell- or tissue-containing devices (collectively may be called "cell-containing devices") have recently been studied for implantation therapy. Cell-containing devices are, for example, capable of holding living cells or tissue to supply hormones, proteins or other physiologically active substances involved in metabolic functions to a patient or to detoxify harmful substances in a patient body, thereby serving as an alternative organ in a human or animal patient suffering from a disease to prevent and/or treat the disease.

These devices may be composed of cells or tissue and serve as a cell- or tissue-containing device, and may further contain an immunoisolation layer or an immunoisolation function containing or embedding cells or tissue therein and serve as a device capable of transplanting cells or tissue embedded in an immunoisolation layer.

The devices having such an immunoisolation layer are advantageous in various aspects. For example, the immunoisolation layer is capable of protecting living cells or tissue from the immune defense system in the body, and hence the devices do not require administration of immunosuppressive drugs, in contrast to direct transplantation of cells or tissue, for example, living donor organ transplantation. The devices can therefore avoid adverse side effects associated with immunosuppressive drugs. The devices can also be implanted in a patient body in a less invasive manner. Lastly, the devices can solve the problem of organ donor shortage.

Such devices having an immunoisolation function may be in various forms, such as those in the form of a microcapsule or a macrocapsule formulation that encapsulates living cells or tissue in a polymer (e.g., a cell formulation). These types of devices have a strongly crosslinked polymer structure that is capable of protecting the cells or tissue from the immune defense system in the body. The devices also utilize the molecular permeability of the polymer to supply hormones or other substances secreted from the cells or tissue to the body of the recipient.

Several such devices are proposed in literature. For example, Patent literature 1 discloses a cell- or tissue-embedding device having an aqueous gel serving as an immunoisolation layer, the aqueous gel containing a modified polyvinyl alcohol resin having an active carbonyl group (A) and a crosslinking agent (B). Patent literature 2 discloses a cell- or tissue-embedding device having an aqueous gel serving as an immunoisolation layer, the aqueous gel containing a polyvinyl alcohol resin having a triad syndiotacticity of 32 to 40% (A).

However, living cells or tissue contained in these devices may not be supplied with sufficient oxygen or nutrients. The shortage of supply of oxygen or nutrients may be more noticeable for cell-containing devices containing naked living cells or tissue embedded in an immunoisolation layer. Live cells or tissue not supplied with sufficient oxygen or nutrients may cause central necrosis, and implantation of the cell-containing devices may become less effective, or the functions of the cell-containing devices may be severely deteriorated.

Such a problem often occurs when the devices are implanted in subcutaneous regions where blood vessels are not abundant. More severe shortage of oxygen or nutrients in subcutaneous regions will occur in large animals having thicker subcutaneous tissue.

To solve the problem of shortage of oxygen and nutrients, use of a cell growth factor has been proposed to induce angiogenesis in the transplantation site of live cells. For example, Patent literature 3 discloses use of a gelatin hydrogel containing a basic fibroblast growth factor.

CITATION LIST

Patent Literature

Patent literature 1: WO 2018/155621
Patent literature 2: WO 2018/155622
Patent literature 3: JP 2002-145797 A

SUMMARY OF INVENTION

Technical Problem

An object of the present invention is to provide a novel gelatin-containing device and others.

According to the studies conducted by the inventors, induction of angiogenesis only at the implantation site of a cell-containing device results in a small contact area between the cell-containing device and newly formed blood vessels, and oxygen or nutrients may not be efficiently supplied to living cells, living tissue, etc.

When angiogenesis is induced using cell growth factors, the blood and exudates from bleeding or inflammation may be accumulated at the angiogenesis site. Such blood and exudates form a liquid membrane between the newly formed blood vessels and cells or the cell-containing device, and the liquid membrane may prevent the diffusion of oxygen and nutrients from the newly formed blood vessels to the cell-containing device and may significantly inhibit the exhibition of the functions of the cell-containing device.

Accordingly, the inventors performed extensive studies focusing on a concept that is completely different from induction of angiogenesis by exogenous administration of growth factors as described in Patent literature 3, and found that implantation or placement of a particular device, material or member comprising a gelatin is capable of activating the implantation site. In particular, the inventors found that, for example, a device comprising a gelatin can be implanted or placed into an implantation site prior to implantation of a cell-containing device into the implantation site, thereby reducing or preventing the problems as described above and allowing the cell-containing device to efficiently exhibit its functions. The inventors conducted further studies and completed the invention.

Thus, the present invention relates to the following and others.

[1]

An implantation device (an implantation material or an implantation member) comprising a bioabsorbable non-woven fabric containing a gelatin or a biocompatible non-woven fabric containing a gelatin.

[2]

The device according to the above [1], wherein the non-woven fabric has been subjected to crosslinking.

[3]

The device according to the above [1] or [2], wherein the non-woven fabric has a compressive deformation of 40% or less as measured when the non-woven fabric in a water-swollen state is compressed with a stress of 1.0 kPa.

[4]
The device according to any one of the above [1] to [3], wherein the non-woven fabric has a visible light transmittance of 10% or more as measured on the non-woven fabric in a water-swollen state.

[5]
The device according to any one of the above [1] to [4], wherein the non-woven fabric has a water content of 300% by mass or less, for example, 200% by mass or less, 100% by mass or less, 20 to 150% by mass, 30 to 100% by mass, 40 to 78% by mass, etc., as measured on the non-woven fabric in a water-swollen state.

[6]
The device according to any one of the above [1] to [5], wherein the non-woven fabric has a diameter that varies in the longitudinal direction of the non-woven fabric.

[7]
The device according to any one of the above [1] to [6], wherein fibers in the non-woven fabric are partially fusion bonded at intersections of the fibers.

[8]
The device according to any one of the above [1] to [7], wherein the non-woven fabric has a mean fiber diameter (D) of 1 to 70 μm, and wherein the mean fiber diameter varies within a range of $D-0.5D \leq D \leq D+0.5D$.

[9]
The device according to any one of the above [1] to [8], wherein the non-woven fabric forms at least part of a surface of the device or is partially exposed on a surface of the device.

[10]
The device according to any one of the above [1] to [9], wherein the device comprises a non-woven fabric and a non-bioabsorbable material or member.

[11]
The device according to any one of the above [1] to [10], wherein the device comprises a non-woven fabric and a non-bioabsorbable material or member, and wherein the non-woven fabric is integrated with the non-bioabsorbable material or member.

[12]
The device according to any one of the above [1] to [11], wherein the device comprises a non-woven fabric and a non-bioabsorbable material or member, and wherein the non-bioabsorbable material or member is contained in an amount of 1 part by volume or more relative to 100 parts by volume of the non-woven fabric.

[13]
The device according to any one of the above [1] to [12], wherein the device comprises a non-woven fabric and a non-bioabsorbable material or member, wherein the non-woven fabric is integrated with the non-bioabsorbable material or member, wherein the non-bioabsorbable material or member is contained in an amount of 10 parts by volume or more relative to 100 parts by volume of the non-woven fabric, and wherein the non-woven fabric forms at least part of a surface of the device or is partially exposed on a surface of the device.

[14]
The device according to any one of the above to [13], wherein the non-bioabsorbable material or member has an adhesion preventive ability.

[15]
The device according to any one of the above [1] to [14], wherein the device is free of or substantially free of growth factors.

[16]
The device according to any one of the above [1] to [15], wherein the device is used for at least one application selected from the following (1) to (3):
    (1) formation of an encapsulating membrane,
    (2) increase of the amount of extracellular matrix, or promotion of secretion of extracellular matrix, and
    (3) increase of the level of a growth factor, or promotion of secretion of a growth factor.

[17]
The device according to the above [16], wherein the extracellular matrix contains at least one selected from collagens, such as collagen III and collagen IV, and laminins.

[18]
The device according to the above or [17], wherein the growth factor contains at least IGF-2.

[19]
The device according to any one of the above to [18], wherein the amount of the extracellular matrix and/or the level of the growth factor is increased in the encapsulating membrane formed, or wherein the device is used for formation of an encapsulating membrane having an increased amount of extracellular matrix and/or an increased level of a growth factor.

[20]
The device according to any one of the above to [19], wherein the device is for use for the applications of (1), (2) and (3).

[21]
The device according to any one of the above [1] to [20], wherein the device is for implantation (or implantation or placement for a predetermined period of time) into an implantation site of a cell- or tissue-containing device, optionally prior to implantation of the cell- or tissue-containing device.

[22]
The device according to any one of the above [1] to [21], wherein the device is for use in combination with a cell- or tissue-containing device.

[23]
The device according to the above or [22], wherein the cell- or tissue-containing device has an immunoisolation layer containing a polyvinyl alcohol resin (A).

[24]
The device according to any one of the above to [23], wherein the cell- or tissue-containing device comprises an immunoisolation layer containing at least one or more polyvinyl alcohol resins (A) selected from a modified polyvinyl alcohol resin having an active carbonyl group (A1), a polyvinyl alcohol resin having a triad syndiotacticity of 32 to 40% (A2), and a polyvinyl alcohol resin having a degree of saponification of 97 mol % or more (A3).

[25]
The device according to any one of the above to [24], wherein the cell or tissue contains at least one selected from a pancreatic islet or islet cells, hepatocytes, stem cells that give rise to islet cells or hepatocytes, and progenitor cells that give rise to islet cells or hepatocytes.

[26]
A method for implanting (or implanting or placing for a predetermined period of time) the device according to any one of the above [1] to [25].

[27]

A method for activating an implantation site, comprising implanting (or implanting or placing for a predetermined period of time) the device according to any one of the above [1] to into the implantation site.

[28]

A method for allowing a non-woven fabric or part of a non-woven fabric to be biologically absorbed in an implantation site or the method according to the above or [27], comprising implanting (or implanting or placing for a predetermined period of time) the device according to any one of the above [1] to into the implantation site.

[29]

A method for performing at least one selected from the following (1) to (3) at an implantation site or the method according to any one of the above to [28], comprising implanting (or implanting or placing for a predetermined period of time) the device according to any one of the above [1] to into the implantation site:

(1) formation of an encapsulating membrane, (2) increase of the amount of extracellular matrix, or promotion of secretion of extracellular matrix, and (3) increase of the level of a growth factor, or promotion of secretion of a growth factor.

[30]

A method comprising implanting (or implanting or placing for a predetermined period of time) the device according to any one of the above to into an implantation site, and retrieving at least a non-bioabsorbable material or member from the implantation site, and optionally creating an implantation spot.

[31]

The method according to the above [30], wherein the device is retrieved without causing bleeding, inflammation and/or rupture of a blood vessel, and wherein an implantation spot is optionally created.

[32]

An implantation method comprising implanting a cell- or tissue-containing device into a site in which the device according to any one of the above [1] to has been implanted and subsequently retrieved.

[33]

A method for preventing and/or treating a disease or a symptom, comprising implanting a cell- or tissue-containing device into a site in which the device according to any one of the above [1] to has been implanted and subsequently retrieved.

[34]

The method according to the above or [33], further comprising implanting the device according to any one of the above [1] to [25], and optionally retrieving at least a non-bioabsorbable material or member, and optionally creating an implantation spot.

[35]

The device or method according to any one of the above [1] to [34], wherein the implantation site is a subcutaneous site or subcutaneous tissue.

Advantageous Effects of Invention

The present invention provides a novel device containing a gelatin.

The device of the invention is capable of activating an implantation site or a placement site.

For example, the device of the invention can be implanted or placed into an implantation site prior to implantation of a cell-containing device into the implantation site, thereby reducing or preventing the problems as described above and allowing the cell-containing device to efficiently exhibit its functions.

The device of the invention is also capable of forming an encapsulating membrane at the implantation or placement site or the neighboring site. Unexpectedly, the device of the invention is also capable of increasing the amount of endogenous extracellular matrix (ECM) and the levels of endogenous growth factors or promoting the secretion of endogenous extracellular matrix (ECM) and endogenous growth factors at the implantation site or the neighboring site.

The reason why the device of the invention is capable of efficiently activating the implantation site as described above remains unclear. However, probably, the gelatin that is arranged in a particular structure, i.e., in the form of a non-woven fabric structure, efficiently exhibits its effects and contributes to the activation of the implantation site due to unknown mechanisms. For example, cells and tissue at the implantation site may be easily incorporated or taken up into the non-woven fabric structure, which may allow the gelatin to easily demonstrate its functions. The non-woven fabric structure also tends to attract effector cells and other cells that secrete growth factors. Such activation probably contributes to increase of the amount of endogenous extracellular matrix (ECM) and the levels of endogenous growth factors or to promotion of the secretion of endogenous extracellular matrix (ECM) and endogenous growth factors.

Due to these functions, the device of the invention is suitable for use as an implantation device or a device for implantation of another device. In particular, the device of the invention can also be used as a device for forming an encapsulating membrane or for increasing the amount of extracellular matrix and the levels of growth factors or promoting the secretion of extracellular matrix and growth factors, etc.

The device of the invention can be used for any applications. The device of the invention can be used for the desired applications, e.g., repair of an injury, e.g., repair of tissue after surgery, etc., depending on the desired degree of activation or the desired manner, including induction of formation of an encapsulating membrane, induction of increase of the amount of extracellular matrix and the levels of growth factors, or induction of promotion of secretion of extracellular matrix and growth factors, etc.

The device of the invention is especially suitable as a device to be implanted (or to be implanted or to be placed for a predetermined period of time) into an implantation site of a cell-containing device, optionally prior to implantation of the cell-containing device.

The device of the invention used in this manner allows the cell-containing device to efficiently exhibit its functions or improves the functions of the cell-containing device. Such enhancement or improvement of the functions of the cell-containing device by the device of the invention is highly reproducible or highly accurate.

The reason why the device of the invention is capable of enhancing or improving the functions of the cell-containing device remains unclear. However, for example, the device of the invention is capable of forming an encapsulating membrane. The encapsulating membrane facilitates close contact between the cell-containing device and the implantation site, and facilitates the efficient supply of oxygen and nutrients to living cells or tissue in the cell-containing device. In this manner, the device of the invention allows the cell-containing device to effectively exhibit its functions or improves the functions of the cell-containing device.

Another factor that deteriorates the functions of the cell-containing device would be related to ECM, e.g., loss of ECM. The device of the invention is capable of increasing the amount of ECM or promoting the secretion of ECM to supply ECM. Probably in this manner, the device of the invention inhibits or prevents reduction in the functions of the cell-containing device.

Another factor that deteriorates the functions of the cell-containing device would be related to induction of apoptosis by hypoxic environment, which is typically found in a subcutaneous site, etc. The device of the invention is capable of increasing the level of a growth factor or promoting the secretion of a growth factor, e.g., IGF-2 etc., thereby inhibiting apoptosis. Probably in this manner, the device of the invention inhibits or prevents reduction in the functions of the cell-containing device.

Growth factors may tend to contribute to induction of angiogenesis. This also probably allows the cell-containing device to efficiently exhibit its functions.

The growth factors and ECM that are induced to increase or secrete by the implantation of the device of the invention are so-called endogenous growth factors and ECM. Such endogenous growth factors and ECM are completely different from exogenous growth factors and ECM, which are, for example, administered or introduced from outside the body using a device containing a growth factor as described in Patent literature 3.

In exogenous administration of growth factors, control of the release rate of growth factors is difficult, including sustained release and local administration, and the growth factors may diffuse from the implantation site to the systemic circulation. Accordingly, a large dose of growth factors may be required, or unexpected adverse side effects, e.g., induction of bleeding, swelling or tumorigenic transformation, may occur. However, in endogenous administration of ECM and growth factors, a suitable amount of ECM and growth factors are continuously produced or released at the required timing in accordance with the principle of homeostasis. As a result, the problems as described above can be efficiently reduced or prevented, and the amount of ECM or the levels of growth factors can be increased with high reproducibility.

Another disadvantage of exogenous administration of ECM and growth factors is that targeted local increase or abundance of both of ECM and growth factors at an implantation site is difficult to achieve. The device of the invention is, however, capable of locally increasing both of ECM and growth factors, which together may efficiently activate the implantation site. When a cell-containing device is subsequently implanted, the ECM and growth factors together may improve the functions of the cell-containing device.

The device of the invention is also useful in that the device is capable of being implanted into even a blood vessel-poor site, e.g., a subcutaneous site, in which a cell-containing device or other types of devices are assumed not to fully exhibit their functions, and the device of the invention is also capable of activating such a blood-vessel poor site. For example, the device of the invention is capable of activating the implantation site of a cell-containing device as described above, in particular, the device of the invention is capable of activating the implantation site of a cell-containing device and forming an encapsulating membrane and increasing ECM and a growth factor. Probably due to these mechanisms, the device of the invention is capable of efficiently inhibiting or preventing central necrosis and greatly improving the functions of a cell-containing device, regardless of the abundance or scarcity of blood vessels or the presence or absence of angiogenesis at the implantation site.

The device of the invention does not require administration of exogenous growth factors or other factors as described above or subsequent angiogenesis by such exogenous growth factors or other factors, and is capable of efficiently preventing the accumulation of blood or exudates caused by bleeding or inflammation at the implantation site. The device of the invention therefore allows a cell-containing device or another device to fully exhibit its functions.

The device of the invention itself can induce angiogenesis at the implantation site as described above, but this angiogenesis is induced by endogenous factors, and the degree of angiogenesis is smaller and less excessive than that induced by exogenous administration of growth factors. Therefore, even when bleeding or the like occurs, such bleeding or the like can usually be inhibited or prevented at a high level.

According to another aspect of the invention, the device of the invention comprises a non-bioabsorbable material. The non-bioabsorbable material may serve as a spacer in the device, or may have a spacer-like function. When such a device of the invention comprising a non-bioabsorbable material is implanted or placed in a body, at least the non-bioabsorbable material is usually not absorbed but remains in the body. Therefore, after retrieval of the device of the invention, a vacant space can be efficiently formed at the location where the non-bioabsorbable material has been placed, and serves as an implantation pocket.

Such an implantation pocket makes it easier to implant or locate a cell-containing device or the like in the body.

The device of the invention comprising such a non-bioabsorbable material can typically be efficiently retrieved. For example, typically, the device of the invention rarely develops adhesions to the implantation site or an encapsulating membrane formed or the surrounding sites. When the device of the invention is retrieved, the device rarely causes damage to these sites or the encapsulating membrane. In this manner, the device is capable of preventing or reducing bleeding, inflammation (induction of inflammation) or release of exudates from the implantation site etc. The device of the invention comprising such a non-bioabsorbable material is adapted to induce the activation of the implantation site, including formation of an encapsulating membrane, and is also adapted to facilitate the retrieval of the device, and is thus very useful.

DESCRIPTION OF EMBODIMENTS

Device

The device of the invention (may also be called the device 1, the gelatin-containing device, the material, the member, etc.) comprises a non-woven fabric containing a gelatin, i.e., gelatin-containing non-woven fabric.

Non-Woven Fabric

The non-woven fabric contains a gelatin (may be called the gelatin (A) etc.). Such a gelatin-containing non-woven fabric may typically be made or formed of fibers containing a gelatin.

The gelatin may be any type of gelatin or may be derived from any animal, such as fish, bovines or pigs, or may be a recombinant, e.g., a recombinant gelatin, a human recombinant gelatin, etc.

The gelatin may be produced by any method, including, e.g., alkaline treatment or acid treatment, etc.

The isoelectric point, molecular weight, molecular weight distribution, viscosity, jelly strength, etc., of the gelatin are not limited to particular ones and may be selected as appropriate.

The gelatin may be modified or derivatized. For example, a hydrophobic group, e.g., a hydrocarbon group, such as an alkyl group, may be introduced in the gelatin. For example, the amino groups of the gelatin may be acylated. For example, the amino groups of the gelatin may be subjected to alkanoylation such as hexanoylation and dodecanoylation. The gelatin may not be modified or derivatized.

The modifications or derivatizations may be introduced into any site of the gelatin molecule, and may be introduced into a molecular terminal or a side chain, etc. Such modifications or derivatizations are usually introduced to the extent or degree that the bioabsorbability of the gelatin is not deteriorated before and after the modifications or derivatizations.

A gelatin suitable for use in inhibition of inflammation or swelling at the implantation site includes a gelatin without any modifications or chemical modifications; an underivatized gelatin, e.g., a gelatin without any introduction of hydrophobic groups, etc.; a gelatin with a small amount of modifications or chemical modifications; or a gelatin with a low degree of derivatization, e.g., a gelatin with introduction of a small amount of hydrophobic groups, etc., e.g., a gelatin in which about 20 mol % or less, e.g., 10 mol % or less, 5 mol % or less, or 3 mol % or less of the total amino groups is modified or derivatized.

The non-woven fabric or the fibers constituting the non-woven fabric may typically be biocompatible or bioabsorbable. The non-woven fabric may typically be bioabsorbable and may also be biocompatible. Such a non-woven fabric may be understood to contain a gelatin as a bioabsorbable material or to be a non-woven fabric containing a gelatin as a bioabsorbable material.

The non-woven fabric or the fibers constituting the non-woven fabric comprise at least a gelatin or a gelatin serving as a bioabsorbable material, and may further contain an additional material as needed.

Such an additional material may also typically be biocompatible or bioabsorbable.

The additional material serving as a bioabsorbable material may be, for example, a protein or peptide, e.g., a collagen or a collagen peptide; a polysaccharide or its derivative, such as a mucopolysaccharide, e.g., hyaluronic acid or heparin, alginic acid, chitin, chitosan, starch, dextran, etc.; or an aliphatic polyester, such as polyglycolic acid, polylactic acid, a glycolic acid/lactic acid copolymer, poly-β-hydroxybutyrate, etc.

These additional materials may be used alone or in combination of two or more types.

When the device of the invention contains the additional material serving as a bioabsorbable material, the amount of the gelatin relative to the amount of the non-woven fabric (or relative to the fibers constituting the non-woven fabric, the bioabsorbable material or the bioabsorbable polymer) may be, for example, 30% by mass or more, 50% by mass or more, 70% by mass or more, 80% by mass or more, 90% by mass or more, 95% by mass or more, etc., although the amount of the gelatin will depend on the type of additional material or other factors.

The non-woven fabric, the device, the gelatin or the bioabsorbable material may contain an additional component. The additional component may be, for example, but is not limited to, a cell culture component, such as an alkali metal, an alkaline earth metal, a halogen, glucose, or a physiologically active substance, etc. as described later.

The additional component may be an angiogenic component, or a component capable of contributing to angiogenesis.

The angiogenic component or a component capable of promoting angiogenesis may be any component that contributes to or promotes angiogenesis. Examples of such a component include growth factors or cell growth factors, such as vascular endothelial growth factor (VEGF), fibroblast growth factor (FGF), hepatocyte growth factor (HGF), epidermal growth factor (EGF), insulin-like growth factor (IGF) (e.g., IGF-1, IGF-2, etc.), platelet-derived growth factor (PDGF), placental growth factor (PlGF) and insulin; and cells, such as cells capable of secreting growth factors or cell growth factors.

Examples of the cells include stem cells such as mesenchymal stem cells (MSCs), including, for example, adipose-derived stem cells (ADSCs), marrow-derived stem cells (BMSCs), placenta-derived stem cells, and umbilical cord-derived stem cells.

The non-woven fabric, the device, the gelatin or the bioabsorbable material may be free of or may be substantially free of such an additional component, e.g., an angiogenic component, and in particular, may be free of or may be substantially free of growth factors.

The device, the non-woven fabric, the gelatin or the bioabsorbable material of the invention may be capable of activating the implantation site as described above. In particular, the device, the non-woven fabric, the gelatin or the bioabsorbable material of the invention is capable of activating the implantation site and forming an encapsulating membrane and increasing the amount of extracellular matrix or the levels of growth factors or promoting the secretion of extracellular matrix and growth factors, etc. Therefore, the activation of the implantation site can be achieved without inducing angiogenesis by growth factors, or the activation of the implantation site can be achieved in a different manner from angiogenesis by growth factors.

Use or administration of exogenous growth factors also differs from use of cells (ADSCs) etc. in that administration of exogenous growth factors may induce damage such as bleeding, inflammation and accumulation of blood and exudates due to angiogenesis or excessive or extreme angiogenesis. Such damage may also reduce the functions and/or the implantation performance of a cell-containing device as described later. However, growth factors are not used in the invention, and such damage can efficiently be reduced or prevented.

The non-woven fabric or the fibers constituting the non-woven fabric or the gelatin is preferably subjected to crosslinking.

Crosslinking treatment enhances the strength of the non-woven fabric serving as a bioabsorbable material and promotes the biological absorption of the non-woven fabric over a predetermined period of time, e.g., over one week to three months. Probably due to the enhancement of the strength of the non-woven fabric and the promotion of the biological absorption of the non-woven fabric, crosslinking treatment on the non-woven fabric is advantageous for the activation of the implantation site, in particular, for the activation of the implantation site accompanied by formation of an encapsulating membrane or a uniform, encapsulating membrane and promotion of secretion of ECM or a growth factor, and is also advantageous for allowing a cell-containing device to exhibit its functions, etc.

The crosslinking method may be, but is not limited to, crosslinking using a chemical reagent, e.g., crosslinking using a crosslinking agent, e.g., an aldehyde such as form-aldehyde or glutaraldehyde, or a carbodiimide; crosslinking by heating, such as thermal dehydration crosslinking or thermal crosslinking; enzymatic crosslinking; crosslinking by energy rays, such as optical crosslinking, ultraviolet rays, electron rays or radioactive rays; physical crosslinking via, e.g., hydrogen bonds, hydrophobic interactions, ionic inter-actions, etc.; etc. Preferred among these is crosslinking by heating, such as thermal dehydration crosslinking etc.

The fibers constituting the non-woven fabric may typi-cally be filaments. The length of the filaments may be, but is not limited to, for example, about several tens meters to several hundreds meters.

The diameter or mean diameter (D) of the fibers or filaments constituting the non-woven fabric may be, for example, about 1 to 70 µm, for example, about 5 to 60 µm.

The diameter of the fibers may be constant or remain the same in the longitudinal direction of the fibers, or may vary or be changeable in the longitudinal direction of the fibers. When the diameter of the fibers varies in the longitudinal direction of the fibers, the diameter of the fibers or the mean fiber diameter may vary, for example, within a range of $D-0.5D \leq D \leq D+0.5D$.

The non-woven fabric with the characteristics as described above is easily adapted to be biologically absorbed within a preferred period of time, e.g., within one week to three months. The non-woven fabric tends to be easily biologically absorbed with its structure maintained, and therefore the effects of the non-woven fabric structure are easily exhibited. For example, cells and tissue at the implantation site may be easily incorporated or taken up into the non-woven fabric structure.

Even when the non-woven fabric or the fibers constituting the non-woven fabric are wet with water, the non-woven fabric or the fibers generally remain firm.

In particular, the compressive deformation of the non-woven fabric in a water-swollen state or in a swollen state by absorbing water up to its saturation is preferably, but not limited to, 40% or less, more preferably 35% or less, particularly preferably 30% or less, as measured when the non-woven fabric in a water-swollen state is compressed with a stress of 1.0 kPa. The lower limit of the compressive deformation is preferably, but not limited to, 1% or more, more preferably 5% or more.

The compressive deformation is calculated from the thickness of the non-woven fabric under no load conditions (H1) and the thickness of the non-woven fabric compressed with a stress of 1.0 kPa (H2) using the following equation:

$$\text{Compressive deformation (\%)} = 100 - \{(H2/H1) \times 100\}.$$

The compressive deformation of the non-woven fabric is, for example, determined after immersion of the non-woven fabric in water at 37° C. overnight, e.g., for 16 hours, and can be measured using a physical property testing system, a creep meter RE2-33005C (Yamaden Co., Ltd.).

The fibers in the non-woven fabric may be fusion bonded at intersections of the fibers. The fibers may be at least partially melt bonded or fusion bonded, or the fibers may be melt bonded or fusion bonded at all intersections of the fibers.

The non-woven fabric with such characteristics, i.e., the non-woven fabric that remains firm even when wet with water, exhibits good handling at the time of implantation and is easily arranged or located at the targeted site, and pro-motes the formation of an encapsulating membrane, etc.

The non-woven fabric may appear transparent or rela-tively transparent when the non-woven fabric is wet with water or swollen with water.

In particular, the visible light transmittance of the non-woven fabric in a water-swollen state or in a swollen state by absorbing water up to its saturation is preferably, but not limited to, 10% or more, more preferably 15% or more, particularly preferably 20% or more.

The visible light transmittance of the non-woven fabric is, for example, determined after immersion of a non-woven fabric sample of 1.0 mm in thickness in water at 37° C. overnight, e.g., for 16 hours, and can be determined by measuring an average transmittance of light at a wavelength from 400 to 800 nm through the swollen fabric sample using SYNERGY H1 (BioTek).

The non-woven fabric with such characteristics easily absorbs the body fluid thereinto and is biologically absorbed relatively uniformly and exhibits other effects, thereby effi-ciently activating the implantation site.

The water content of the non-woven fabric in a water-swollen state or in a swollen state by absorbing water up to its saturation may, for example, be selected from the range of about 300% by mass or less, or may be 200% by mass or less, e.g., 180% by mass or less, or may preferably be about 150% by mass or less, e.g., 120% by mass or less, or 100% by mass or less, e.g., 90% by mass or less, 85% by mass or less, 80% by mass or less, 78% by mass or less, 77% by mass or less, 76% by mass or less, 75% by mass or less, etc.

The lower limit of the water content of the non-woven fabric in a water-swollen state may, for example, be 10% by mass, 20% by mass, 30% by mass, 40% by mass, 50% by mass, 55% by mass, 60% by mass, 70% by mass, etc.

In particular, the water content of the non-woven fabric in a water-swollen state may be within the range defined by the upper and lower limit values as described above, and may, for example, be 10 to 200% by mass, 20 to 150% by mass, 30 to 100% by mass, 40 to 78% by mass, etc.

The water content of the non-woven fabric in a water-swollen state is determined as follows. For example, the non-woven fabric is first immersed in or allowed to swell with water at 37° C. for a sufficient period of time, e.g., overnight, e.g., for 16 hours or 24 hours, etc. and the mass of the non-woven fabric is measured. The water content of the non-woven fabric immersed in or swollen with water is then calculated by the equation below using the mass (Wh) of the non-woven fabric measured after immersed in or swollen with water, and the mass (dry weight) (Ws) of the non-woven fabric measured before immersed in or swollen with water.

$$\text{Water content (\%)} = (Wh - Ws)/(Wh) \times 100$$

The non-woven fabric with such a water content is easily adapted to be biologically absorbed within a preferred period of time, e.g., within one week to three months, thereby efficiently activating the implantation site. The non-woven fabric tends to be easily biologically absorbed with its structure maintained, and therefore the effects of the non-woven fabric structure are easily exhibited. For example, cells and tissue at the implantation site may be easily incorporated or taken up into the non-woven fabric structure.

The non-woven fabric may be in any shape, and may be in the shape of, for example, but not limited to, a sheet, a plate or a disk, a bar, a tube, granules or beads, etc.

The size of the non-woven fabric may be selected as appropriate from the range as described above depending on the implantation site or its size, etc. For example, the thickness of the non-woven fabric is preferably 0.1 to 10 mm, more preferably 0.2 to 5 mm, further preferably 0.5 to 2 mm, and particularly preferably 0.7 to 1.5 mm.

Production Method of Non-Woven Fabric

The production method of the non-woven fabric, in particular, a filament non-woven fabric, is not limited to a particular one and may be a known method. The production method will be described in detail below.

The non-woven fabric can be produced by a known or conventional technique. For example, the non-woven fabric may be produced by the melt blown method as described below.

A spinning solution containing a gelatin is extruded through discharge nozzles surrounded by high-pressure fluid ejected forward from fluid ejection holes arranged behind and not in contact with the discharge nozzles. The spinning solution extruded through the discharge nozzles into air comes into contact with the high-pressure fluid to form fibers. The resulting biocompatible filaments are accumulated to produce a non-woven fabric. A device for producing the non-woven fabric according to the present invention comprises a means for extruding a spinning solution containing a gelatin through discharge nozzles into air; a means for ejecting high-pressure fluid forward from fluid ejection holes arranged behind and not in contact with the discharge nozzles; and a means for accumulating bioabsorbable fibers formed from the spinning solution that is extruded through the discharge nozzles into air and then comes into contact with the high-pressure fluid. The high-pressure fluid ejection holes are arranged independently of the discharge nozzles and disposed behind and not in contact with the discharge nozzles so that the spinning solution is prevented from entering the fluid-ejection holes. In this manner, contamination of the product is prevented.

The temperature of the spinning solution is preferably higher than or equal to the temperature at which the spinning solution flows and less than the decomposition temperature of the gelatin. In order to spin the spinning solution, the temperature of the spinning solution should be higher than or equal to the temperature at which the spinning solution flows. If the temperature of the spinning solution is higher than or equal to the decomposition temperature of the gelatin, decomposed products may contaminate the product.

The ejection pressure of the high-pressure fluid is preferably 0.05 to 0.5 MPa. The high-pressure fluid in this pressure range is capable of blowing the spinning solution extruded through the discharge nozzles into air to produce fibers. The temperature of the high-pressure fluid is preferably near the temperature of the spinning solution, and is more preferably within ±50° C. of the temperature of the spinning solution, and is further preferably within ±30° C. of the temperature of the spinning solution. When the spinning solution extruded through the discharge nozzles is blown into air by the high-pressure fluid at this temperature, the spinning solution is not quickly cooled but is formed into fibers while the spinning solution is maintained in a fluid state, and then the drawn fibers are cooled in air to form solid fibers.

The viscosity of the spinning solution at 60° C. is preferably 500 to 3000 mPa·s. The viscosity in this range is advantageous for forming fibers.

The non-woven fabric is preferably subjected to crosslinking. Crosslinking of the fibers of the non-woven fabric is preferred for improving the stability of the shape of the non-woven fabric. Crosslinking is performed as described above. The temperature for crosslinking by heating, such as thermal dehydration crosslinking, is preferably higher than or equal to the glass transition point of the fibers, i.e., the bioabsorbable polymer, such as gelatin, that forms the fibers, and lower than or equal to the softening point of the fibers. The temperature suitable for crosslinking by heating is, for example, 100 to 160° C. The non-woven fabric may be dried prior to crosslinking. Drying may be air drying at room temperature or vacuum freeze-drying.

The non-woven fabric containing a gelatin will be specifically described below.

The production method of a gelatin non-woven fabric or a gelatin filament non-woven fabric may comprise, for example, the following steps.

1. Preliminary Step (1) Dissolve a gelatin in warm water. The temperature for dissolving the gelatin, i.e., the temperature of warm water is preferably 20 to 90° C. After dissolving, the gelatin solution is filtered to remove foreign bodies, impurities, etc.

(2) Dissolved air in the solution may be removed by degassing under reduced pressure or vacuum.

2. Main Step (1) Discharge the heated aqueous gelatin solution (spinning solution) from the nozzles of a spinning machine.

(2) Supply high-pressure fluid from the periphery of the nozzles. The discharged aqueous gelatin solution comes into contact with the high-pressure fluid to form fibers.

(3) The produced gelatin filaments are accumulated to produce a gelatin filament non-woven fabric.

3. Post-Processing Step (1) The resulting gelatin filament non-woven fabric may be dried.

(2) Cut the gelatin filament non-woven fabric into a predetermined size. The non-woven fabric may be formed into a predetermined shape. Forming into a predetermined shape can be performed by press-molding or other techniques.

(3) Crosslink the gelatin filaments of the non-woven fabric. Crosslinking may be done by the crosslinking methods as exemplified above, including thermal dehydration crosslinking, thermal crosslinking, crosslinking by electron rays, radiation crosslinking by, e.g., γ-rays, crosslinking by ultraviolet rays, etc.

(4) Sterilize the gelatin filament non-woven fabric or the gelatin filament non-woven fabric sheet with a predetermined shape. Sterilization may be performed with ethylene oxide gas, water vapor, electron irradiation, radiation irradiation, such as γ-rays, etc. When sterilization is performed with electron irradiation or radiation irradiation such as γ-rays, crosslinking can be performed simultaneously with sterilization.

4. Sterilization at the Time of Use

For medical applications etc., the gelatin filament non-woven fabric may be sterilized using, e.g., ethylene oxide gas, vapor, etc. as a preliminary step for use. The crosslinked gelatin filament non-woven fabric can be sterilized using, for example, vapor.

The temperature of the warmed aqueous gelatin solution (spinning solution) is preferably 20 to 90° C. When the aqueous gelatin solution is warmed to this temperature range, the gelatin is maintained in a stable sol state. The concentration of the gelatin in the warmed aqueous gelatin solution is preferably 30 to 55% by mass relative to 100% by mass of the aqueous gelatin solution. The concentration of the gelatin in the warmed aqueous gelatin solution is more preferably 35 to 50% by mass. When the warmed aqueous gelatin solution is at this concentration, the gelatin is maintained in a stable sol state. The viscosity of the warmed aqueous gelatin solution (spinning solution) is preferably 500 to 3000 mPa·s. When the warmed aqueous gelatin solution has this viscosity, spinning can be stably performed.

The temperature of the high-pressure fluid used to draw the extruded aqueous gelatin solution (spinning solution) is preferably 80 to 120° C. When the high-pressure fluid is heated to this temperature range, spinning can be stably performed although the spinning may be affected by the flow velocity of the high-pressure fluid and the temperature of the ambient atmosphere. The high-pressure fluid is preferably air. The pressure of the high-pressure fluid is preferably 0.1 to 1 MPa.

The produced non-woven fabric may be formed in the desired shape. For example, a predetermined shape may be punched out from the non-woven fabric, and is then used for the device of the invention. At the time of use, the non-woven fabric may be allowed to swell in a given liquid medium etc.

An embodiment and a production method of the non-woven fabric may be according to known non-woven fabrics or known methods, e.g., according to the embodiments described in JP Pat No. 6450894.

Additional Material

The device of the invention comprises the non-woven fabric, and may be made or formed of only the non-woven fabric and may further contain an additional material, i.e., a material other than the non-woven fabric or the bioabsorbable material or a material that is not classified as a non-woven fabric or a bioabsorbable material.

The device of the invention may comprise, among others, at least a non-bioabsorbable material or member as the additional material or member.

The device of the invention may be made or formed of the non-woven fabric and a non-bioabsorbable material and may be implanted or placed in the body. Even when the non-woven fabric is absorbed or dissolved in the body after implantation, the non-bioabsorbable material remains in the body.

After the implanted device or at least the non-bioabsorbable material is retrieved, or after a portion of the device that has not been absorbed in the body, e.g., the non-bioabsorbable material, is retrieved while part or all of the bioabsorbable material is absorbed, the non-bioabsorbable material that is capable of remaining in the body forms a pocket or a space at the implantation site.

Such a pocket can serve as an indicator of the location of the implantation site that has been activated with the formation of an encapsulating membrane etc. and also serves as a pocket (an implantation pocket) into which a cell-containing device (described later) is subsequently implanted. The pocket is thus particularly useful for implantation of another device etc.

The non-bioabsorbable material will be described in detail below.

Non-Bioabsorbable Material

The non-bioabsorbable material typically contains or is made or formed of a non-bioabsorbable polymer.

Examples of the non-bioabsorbable polymer include, for example, silicone resins; polyvinyl alcohol resins; polyvinyl acetal resins; polyurethane resins; fluororesins, such as polytetrafluoroethylene and perfluoroalkoxyalkane; olefin resins, such as polyethylene resins and polypropylene resins; polyacrylamide resins; polyester resins, such as polyethylene terephthalate; polyacrylonitrile resins; polystyrene butadiene copolymer resins; polysulfone resins; cellulose resins, such as cellulose ethers, such as carboxymethyl cellulose and hydroxypropyl cellulose; and polyoxyalkylene resins, such as a resin containing ethylene oxide or propylene oxide as a polymerization component.

The non-bioabsorbable material or the non-bioabsorbable polymer is not absorbed in the body but may typically be biocompatible or a biocompatible polymer. The non-bioabsorbable material or the non-bioabsorbable polymer may be a hydrophilic polymer or a water-soluble polymer. The hydrophilic polymer or the water-soluble polymer contained in the device or the non-bioabsorbable material may typically be converted into a water-insoluble form, e.g., a gel, by crosslinking and/or chemical modifications or other techniques.

The non-bioabsorbable material preferably rarely develops adhesions to the implantation site or the surrounding tissue, i.e., preferably has an adhesion preventive ability. The adhesion preventive ability refers to, for example, the ability to prevent or inhibit the development of adhesions between the device and the surrounding tissue or the encapsulating membrane formed when the device is placed at an implantation site.

A silicone resin, a polyvinyl alcohol resin and others are preferred among the polymers as exemplified above.

A suitable polyvinyl alcohol resin (a polyvinyl alcohol resin (A)) may be a resin as described later, and may be, for example, a modified polyvinyl alcohol resin having an active carbonyl group (A1), a polyvinyl alcohol resin having a triad syndiotacticity of 32 to 40% (A2), a polyvinyl alcohol resin having a degree of saponification of 97 mol % or more (A3), etc.

A preferred embodiment etc. of such a polyvinyl alcohol resin may be the same as those described later.

The device of the invention containing such a non-bioabsorbable material develops few adhesions to the surrounding tissue, and at the time of retrieval, rarely causes damage to the surrounding tissue or the encapsulating membrane formed or a vascular bed at the implantation site, etc. In this manner, the device of the invention is capable of efficiently preventing or reducing bleeding, inflammation (induction of inflammation) or release of exudates from the implantation site, and due to this, the non-woven fabric fully exhibits its functions.

The dissolution rate of the non-bioabsorbable material in physiological saline at 37° C. is preferably, but not limited to, 5% or less, more preferably 3% or less, and particularly preferably 1% or less.

The dissolution rate is, for example, determined after immersion of the non-bioabsorbable material in physiological saline at 37° C. for a predetermined period of time, e.g., 60 minutes, and can be determined by measuring the mass of the solid content of the saline containing the eluted non-bioabsorbable material.

The volume change of the non-bioabsorbable material after immersed in water at 37° C. is preferably, but not limited to, 80% or less, more preferably 70% or less, and particularly preferably 60% or less.

The volume change is, for example, determined after immersion of the non-bioabsorbable material in water at 37° C. for a predetermined period of time, e.g., 60 minutes, and can be determined by measuring the volume before and after the immersion.

The non-bioabsorbable material having the dissolution rate and the volume change as described above easily retains its shape when the device is implanted into the body, and easily produces an implantation pocket with the desired size and/or shape.

The non-bioabsorbable material may typically have an appropriate shape or formed into an appropriate shape.

The form or shape of the non-bioabsorbable material or member may be, for example, but is not limited to, particles or granules, a film or a sheet, a pillar such as a cylinder or a prism, a bar, a tube, etc.

The non-bioabsorbable material may be in the form of fibers, a woven fabric or a non-woven fabric, or may form a woven fabric or a non-woven fabric.

The non-bioabsorbable material may be in the form of a gel, a gum, etc., or may have a porous structure or a sponge structure or a network structure.

For example, the polyvinyl alcohol resin serving as the non-bioabsorbable material may be in the form of a gel, a sponge, etc. A preferred embodiment or physical properties etc. of the polyvinyl alcohol resin serving as the non-bioabsorbable material may be the same as those described later.

The dimension or size of the non-bioabsorbable material can be selected as appropriate for the implantation site or its size and is not limited to a particular one.

For example, the non-bioabsorbable material or a bulky non-bioabsorbable material may have a thickness of 0.01 mm or more, e.g., 0.03 mm or more, preferably 0.05 mm or more, e.g., 0.1 to 50 mm, more preferably 0.15 mm or more, e.g., 0.2 to 10 mm, particularly preferably 0.3 mm or more, e.g., 0.5 to 5 mm or 0.7 to 2 mm, etc.

The non-bioabsorbable material or the non-bioabsorbable polymer may be a commercially available product or may be produced or synthesized by a conventional method, depending on its type or form or its configuration in the device of the invention, etc., but is not limited to a particular one.

For example, the silicone resin serving as the non-bioabsorbable material may be a commercially available silicone rubber sheet or a synthesized silicone rubber sheet.

Alternatively, the polyvinyl alcohol resin serving as the non-bioabsorbable material may be, for example, a commercially available polyvinyl alcohol resin or a synthesized polyvinyl alcohol resin that is formed into a gel, in particular, an aqueous gel or a hydrogel, or a sponge, etc. by a conventional method.

For example, the polyvinyl alcohol resin may be gelled in accordance with the method as described later, e.g., using a crosslinking agent etc., depending on the type of the polyvinyl alcohol resin used. A preferred embodiment of such a polyvinyl alcohol resin may be the same as those described later.

The non-bioabsorbable material, regardless of a commercially available product or a synthesized product, may be formed into the desired shape as appropriate, if needed, in accordance with the shape of the implantation site etc. For example, a predetermined size and/or shape is punched out from the non-bioabsorbable material.

Additional Component

The non-bioabsorbable material or the non-bioabsorbable member may contain an additional component. The additional component is not limited to a particular one, and may be those exemplified in the section of the non-woven fabric.

The non-bioabsorbable material or the non-bioabsorbable polymer may be substantially free of such an additional component, e.g., an angiogenic component, and in particular, may be substantially free of growth factors due to the same reasons as described above.

Device

The device of the invention comprises at least the non-woven fabric and may further comprise an additional material or an additional member as described above.

The device, the non-woven fabric, or an additional material, e.g., a non-bioabsorbable material, may be substantially free of growth factors, as described above.

The non-woven fabric in the device may typically form at least part of a surface of the device, or may be exposed on a surface of the device.

The non-woven fabric may cover 10% or more, e.g., 20% or more, of the surface or surface area of the device, preferably, may cover 30% or more, e.g., 40% or more, of the surface or surface area of the device; more preferably, may cover 50% or more, e.g., 60% or more, of the surface or surface area of the device; or may cover 70% or more, e.g., 80% or more, 90% or more, 95% or more, or (substantially) 100% of the surface or surface area of the device.

When the device contains an additional material, the non-woven fabric and the additional material, in particular, the non-bioabsorbable material, are preferably arranged in such a spatial relationship or a configuration that the non-woven fabric forms at least part of a surface of the device.

When the device contains an additional material, the non-woven fabric may be in contact with or separated from the additional material in the device, but in most cases, the non-woven fabric is typically in contact with the additional material.

Examples of the device with such a configuration include, for example, a device comprising a non-woven fabric covering at least part of a surface of an additional material (the non-bioabsorbable material), for example, a device comprising a sheet-shaped or another shaped non-woven fabric (stacked) on at least one side of a sheet-shaped or another shaped non-bioabsorbable material, in particular, on both sides or the front and back sides of a sheet-shaped or another shaped non-bioabsorbable material; or other devices.

The amount of the additional material (the non-bioabsorbable material) in the device relative to 100 parts by volume of the non-woven fabric may, for example, be 1 part by volume or more, e.g., 5 to 5000 parts by volume; may preferably be 10 parts by volume or more, e.g., 15 to 3000 parts by volume; may more preferably be 20 parts by volume or more, e.g., 25 to 1000 parts by volume; may be 30 parts by volume or more, e.g., 35 parts by volume or more, 40 parts by volume or more, 45 parts by volume or more, etc.; or may be 800 parts by volume or less, e.g., 500 parts by volume or less, 400 parts by volume or less, 300 parts by volume or less, 200 parts by volume or less, 150 parts by volume or less, etc.

When the additional material is contained in such an amount relative to that of the non-woven fabric in the device, a good balance is achieved between the activation (formation of an encapsulating membrane etc.) of the implantation site and the formation of an implantation pocket.

The non-woven fabric and the additional material in the device may typically be fixed to each other, or fixed to each other so that they are integrated together. Typically, the non-woven fabric may be fixed to the additional material (the non-bioabsorbable material), or the non-woven fabric and the additional material (the non-bioabsorbable material) may be fixed to each other. When the non-woven fabric is fixed to the non-bioabsorbable material, the location of the site of activation (the site of formation of an encapsulating membrane etc.) can be easily and efficiently matched with, corresponded to or defined relative to the location of an implantation pocket.

The fixing method may be, for example, but is not limited to, suturing, e.g., suturing with a suture, etc.; sticking, e.g., sticking or pasting with medical glue; etc. A suitable fixing method among these is suturing. The suture and the glue may be biocompatible and/or bioabsorbable or biodegradable.

The non-woven fabric and/or the additional material (the non-bioabsorbable material) may be allowed to swell in water or a given liquid medium selected depending on the type of fabric and/or material. In cases where the fabric and/or the material is allowed to swell in water or a given liquid medium, the fabric and the material may be combined before or after the fabric and the material is allowed to swell in water or a given liquid medium.

Applications Etc.

The device, material or member of the invention can be implanted, in particular, can be implanted in a living body, or can be used for implantation or can be used for implantation of another device etc.

By implanting or placing the device of the invention, the implantation site can be activated.

In particular, by implanting the device of the invention, the following may be induced:

(1) formation of an encapsulating membrane, (2) increase of the amount of extracellular matrix, or promotion of secretion of extracellular matrix, (3) increase of the level of a growth factor, or promotion of secretion of a growth factor, etc.

Due to these effects, the device, material or member of the invention is suitable for use as a device for implantation of another device etc., an implantation device, an implantation material or an implantation member. Such a device capable of activating the implantation site can be used for at least one of the applications as described above.

The device of the invention is generally capable of forming at least an encapsulating membrane, and can typically be used as a device at least for (1) formation of an encapsulating membrane.

The formation of an encapsulating membrane as described in the above (1) can be identified visually or other means by comparing the implantation site before and after the implantation. The encapsulating membrane is typically formed at the implantation site of the device or the bioabsorbable material or its neighboring site or periphery. The encapsulating membrane may be made of at least the gelatin of the device or the non-woven fabric, or the gelatin that is absorbed in the body, or may be made of at least the non-woven fabric or the bioabsorbable material.

The extracellular matrix as described in the above (2) may be, for example, a collagen, such as collagen III or collagen IV; a laminin; etc.

The extracellular matrix may be a single type or a combination of two or more types.

Increase of the amount of extracellular matrix or promotion of secretion of extracellular matrix can be determined by, for example, immunohistochemical assay.

Immunohistochemical assay will be briefly described below. Cells or a cell-containing device is implanted and then the surrounding tissue is harvested. The tissue is fixed in 4% paraformaldehyde and embedded in paraffin. An antibody suitable for immunohistochemical staining includes, for example, anti-collagen III (ab7778; Abcam), anti-collagen IV (ab6586; Abcam) and anti-laminin (ab11575; Abcam) antibodies. A suitable secondary antibody is EnVision+ System HRP-conjugated polymer rabbit antibody (4003; DAKO). Increase of the amount of extracellular matrix or promotion of secretion of extracellular matrix can be evaluated by determining the positive percentage of collagen III, collagen IV and laminin staining in the surrounding tissue.

Examples of the growth factor or cell growth factor as described in the above (3) include epidermal growth factors (EGF); insulin-like growth factors (IGF) such as IGF-1 or IGF-2; fibroblast growth factors (FGF) such as FGF12; hepatocyte growth factors (HGF); transforming growth factors (TGF) such as TGF-β1; and platelet-derived growth factors (PDGF) such as PDGF-A or PDGF-B.

These growth factors may be used alone or in combination of two or more.

The device of the invention is capable of inducing a high-level increase of IGF-2 or promoting the secretion of a high level of IGF-2, among others.

The device of the invention may also be capable of increasing the amount of or promoting the secretion of (4) a component other than extracellular matrix or a growth factor. Such a component other than extracellular matrix or a growth factor includes, for example, cell adhesion molecules, such as N-cadherin, ICAM-1 or VCAM-1; inducers, such as epithelial-mesenchymal transition inducers, such as c-MET, or hypoxia inducible factor $1a$ subunit (HIF-1α); angiogenesis inhibitors, such as vasohibin 1; CD31; versican; thrombospondin (TSP) 2; etc.

Increase of the level of a growth factor etc., or promotion of secretion of a growth factor etc. can be determined by, for example, real-time PCR.

Real-time PCR will be briefly described below. Cells or a cell-containing device is implanted and then the surrounding tissue is harvested. RNA is extracted from the tissue. Relative gene expression is determined using, for example, TaqMan Array 96-well FAST plates (4413257; Applied Biosystems). TaqMan Array contains 46 target genes and 2 endogenous control gene candidates. Samples are analyzed using StepOnePlus Real-Time polymerase chain reaction (PCR) system (Applied Biosystems) under amplification conditions of 50° C. for 2 min, 95° C. for 20 sec, followed by 40 cycles of 95° C. for 1 sec and 60° C. for 20 sec. The results are analyzed by Expression Suite Software ver. 1.3 (Applied Biosystems). Relative quantification (RQ) is performed by the comparative CT method to evaluate increase of the level of growth factors, or promotion of secretion of growth factors. 18S is used as a housekeeping gene.

The extracellular matrix and the growth factor as well as the component other than extracellular matrix or a growth factor are typically produced at the implantation site of the device, the non-woven fabric, or the bioabsorbable material or its neighboring site or periphery, and may be produced in or within the encapsulating membrane.

The device of the invention may achieve any one of the above (1) to (3) and (4), or may achieve a combination of any one of the above (1) to (3) and (4). When a combination of any one of the above (1) to (3) and (4) as well as angiogenesis as described later are achieved by the device of the invention, various factors in combination exhibit various effects and efficiently activate the implantation site.

The device of the invention can typically be used as a device for implantation as described above.

In particular, the device of the present invention can be implanted or placed in the body of an animal, including a human.

By implanting or placing the device of the invention, the implantation site or the placement site can be activated. For example, the device may be capable of inducing at least one selected from:

(1) formation of an encapsulating membrane, (2) increase of the amount of extracellular matrix, or promotion of secretion of extracellular matrix, and (3) increase of the level of a growth factor, or promotion of secretion of a growth factor.

The device of the invention may be capable of increasing the amount of or promoting the secretion of a component other than extracellular matrix or a growth factor.

The device of the invention may be implanted or placed to induce angiogenesis or formation of new blood vessels. The device of the invention is capable of achieving the activation as described above without exogenous administration of growth factors as described above. As the level of an endogenous growth factor etc. is increased or the secretion of an endogenous growth factor etc. is promoted by the device of the invention, angiogenesis or mild angiogenesis may occur. Such angiogenesis together with the formation of an encapsulating membrane etc. may activate the implantation site.

The degree of angiogenesis may be examined by, for example, immunohistochemical assay, computerized tomography (CT) angiography, or other methods.

For immunohistochemical assay, the device of the invention is implanted and then the surrounding tissue is harvested. The tissue is fixed in 4% paraformaldehyde and embedded in paraffin. A suitable immunohistochemical staining antibody is, for example, an anti-von Willebrand factor (vWF) antibody (ab7356; Merck Millipore). A suitable secondary antibody is EnVision+ System HRP-conjugated polymer rabbit antibody (4003; DAKO). The number of vWF-positive cells or the number of the vWF-positive cells in the stromal region is counted to assess the degree of angiogenesis.

For computerized tomography (CT) angiography, for example, ExiTron nano 12000 is suitable for use, which is an alkaline earth metal-based nanoparticulate contrast agent specifically formulated for CT of animals. The nanoparticulate contrast agent is intravenously injected via the tail vein. Angiography is performed using an X-ray CT scanner for experimental animals (Latheta LCT-200; Hitachi) etc. Angiogenesis can be assessed by calculating the blood vessel volume in the surrounding tissue of cells or a cell-containing device. To extract capillary blood vessels, the CT number for analyzing the vascular region is preferably defined as 100 or more.

The implantation according to the invention is performed using at least the device of the invention, and the device of the invention may be implanted as needed together with another device, for example, together with a device containing a non-bioabsorbable material, such as a polyvinyl alcohol resin or the resin as described later, a device containing a non-bioabsorbable material further containing cells (such as ADSCs) that secrete a growth factor.

The implantation site may be, for example, but is not limited to, a subcutaneous site; a subfascial site; the surface of an organ, e.g., the surface of the liver, spleen or other organs; an intraperitoneal site, e.g., under the greater omentum; under the mesentery; the peritoneal cavity; the inguinal region; etc. The implantation site may be muscular tissue, adipose tissue (adipocytes), etc. The implantation site is preferably a subcutaneous site or subcutaneous tissue.

Subcutaneous sites usually have few blood vessels, but the device of the present invention is capable of efficiently activating such a site with few blood vessels, independently of angiogenesis.

The device of the invention may be implanted or placed in any manner and may be implanted or placed in accordance with a conventional or known method. For example, instruments known to be used for implantation may be employed.

The subject for implantation of the device of the invention and optionally a cell-containing device as described later may be a human or a non-human animal, for example, a mammal such as a dog or a cat. The non-human animal may be a companion animal. A preferred subject is a human.

The duration of placement of the device of the invention may vary depending on the implantation site or other factors, but the implanted device is preferably left at the implantation site for, for example, one week or more, more preferably for 10 days to three months, and particularly preferably for two weeks to two months.

When the device of the invention is left in the implantation site for such a period of time, sufficient activation of the implantation site, including formation of an encapsulating membrane, etc., are easily achieved.

An encapsulating membrane containing a gelatin or a bioabsorbable material from the device or the non-woven fabric is usually formed by the implantation or placement of the device of the invention, as described above. After formation of the encapsulating membrane, the gelatin may be gradually absorbed in the body over time. The duration of placement of the device, or the duration of placement of the device until retrieval of the device may be determined so that at least the encapsulating membrane containing the gelatin, i.e., the encapsulating membrane containing the residual gelatin, is retained in the device.

The implanted device of the invention may be retrieved from the implantation site after a predetermined duration of placement has past. In most cases, when the device of the invention comprising a non-bioabsorbable material is implanted, at least the non-bioabsorbable material, typically, only the non-bioabsorbable material, is retrieved from the implantation site. The present invention also includes such a method for retrieving the device of the invention.

In most cases, when the device of the invention is placed in the body for the predetermined period of time, e.g., for one week to three months, part or all of the non-woven fabric, the gelatin and/or the bioabsorbable material is typically absorbed in the body and forms an encapsulating membrane. However, the non-bioabsorbable material does not absorbed in the body but remains as it is at the implantation site. The non-bioabsorbable material needs to be retrieved when a cell-containing device etc. is subsequently implanted into the implantation site.

The retrieval of the device of the invention and/or the non-bioabsorbable material is usually performed without causing bleeding, inflammation, rupture of existing blood vessels or newly formed blood vessels, damage to the encapsulating membrane or the formed encapsulating membrane, etc. If bleeding, inflammation, rupture of blood vessels or damage to the encapsulating membrane occurs, the blood or exudates may accumulate at the site from which the device and/or the non-bioabsorbable material has been retrieved.

The non-bioabsorbable material as described above, e.g., a silicone resin, a polyvinyl alcohol resin, etc., is selected for use in the present invention, and the duration of placement of the device is also selected as appropriate. Due to these materials and the duration of placement and/or other factors as well as less probability of development of adhesions to the implantation site, the device of the invention and/or the non-bioabsorbable material can usually be efficiently retrieved without causing bleeding, inflammation or rupture of blood vessels.

An implantation pocket is formed at the site from which the device of the invention and/or the non-bioabsorbable material has been retrieved. A cell-containing device etc. may subsequently be implanted into the implantation pocket as described later.

The implantation site of the device of the invention is activated as described above, and another device may subsequently be implanted into the implantation site.

Implantation of a cell- or tissue-containing device as another device will be described in detail below.

Cell- or Tissue-Containing Device

The present invention also includes a method for implanting or placing a device comprising cells or tissue (a cell- or tissue-containing device; may also be called a cell-containing device or a device 2 below).

Implantation of the cell-containing device (the cell-containing component) may be performed in parallel to the implantation or placement of the device of the invention (the device 1 or the gelatin-containing device) or may be performed at the same time of the implantation or placement of the device of the invention (the device 1 or the gelatin-containing device). Alternatively, the implantation of the cell-containing device (the cell-containing component) may not be performed in parallel to the implantation or placement of the device of the invention (the device 1 or the gelatin-containing device) or may not be performed at the same time of the implantation or placement of the device of the invention (the device 1 or the gelatin-containing device).

When the implantation of the cell-containing device is performed in parallel to the implantation of the device 1, the device 1 may be implanted near or at the periphery of the cell-containing device, or may be implanted adjacent to the cell-containing device.

The cell-containing device may be implanted or placed at the site in which the device 1 has been implanted and subsequently the device 1 or at least the non-bioabsorbable material has been retrieved, i.e., at the implantation site or into the implantation pocket.

In either of the cases, when an encapsulating membrane is formed by the device 1, the cell-containing device is preferably implanted after the encapsulating membrane is formed or while the encapsulating membrane is retained or at the time when the encapsulating membrane is formed or retained, in particular, while the gelatin is contained or remains in the encapsulating membrane.

In other words, the device of the invention (the device 1) can be used as a device for use in combination with the cell-containing device, in particular, as a device to be implanted in the implantation site of the cell-containing device or the implantation site that is to be activated, e.g., the implantation site where an encapsulating membrane is to be formed, etc., or as a device to be implanted prior to implantation of the cell-containing device in the implantation site of the cell-containing device or the implantation site that is to be activated, e.g., the implantation site where an encapsulating membrane is to be formed, etc.

The device of the invention (the device 1) is capable of activating the implantation site of the cell-embedding device or the neighboring site or the periphery thereof as described above, thereby allowing the cell-containing device to efficiently exhibit its functions.

In this manner, situations can be avoided where living cells or tissue is implanted before the implantation site is activated, and consequently central necrosis and apoptosis may be efficiently inhibited or prevented, thereby allowing the cell-containing device to exhibit its functions. Replacement of the implanted cell-containing device is also easily performed when it is needed.

The device 1 containing a non-bioabsorbable material can be adapted to rarely develop adhesions to the surrounding tissue and to be retrieved (at least the non-bioabsorbable material can be retrieved) without causing bleeding, inflammation or rupture of blood vessels by selecting the type of non-bioabsorbable material etc., as described above. When the cell-containing device is implanted into such a site from which the device 1 has been retrieved, the cell-containing device can be easily exhibit its functions much more efficiently.

Implantation of the cell-containing device into such a site from which the device 1 has been implanted and subsequently retrieved is understood as meaning that the cell-containing device is efficiently implanted into an implantation site without bleeding, inflammation or rupture of blood vessels.

The inventors studied and found that, when the retrieval of the device 1 is accompanied by bleeding, inflammation and/or rupture of blood vessels, blood and/or exudates may easily accumulate between an implanted cell-containing device and the implantation site. The present invention facilitates the implantation or placement of a cell-containing device at an implantation site without being accompanied by bleeding, inflammation and/or rupture of blood vessels, and also activates the implantation site as described above, thereby allowing the cell-containing device to efficiently exhibit its functions.

Bleeding, inflammation and/or rupture of blood vessels, if occurs, at the implantation site can be visually observed, for example, before and after the implantation or retrieval or harvest of the device 1 or before the implantation of the cell-containing device.

The cell-containing device as described above may be cells or tissue itself, or embedded cells or tissue (may also be called the cell-embedding device below).

The cell-embedding device may be any cell-embedding device and may be, for example, but is not limited to, the cell-embedding device or the like described in Patent literature 1 or 2. The cell-embedding device will be described in detail below.

A biological composition (e.g., cells or tissue) contained in the cell-containing device is not particularly limited and may be selected as appropriate for the purpose of use.

The biological composition may be, for example, differentiated cells, stem cells or other types of cells derived from the ectoderm, mesoderm or endoderm.

The differentiated cells may be, for example, epidermal cells, smooth muscle cells, osteocytes, bone marrow cells, chondrocytes, skeletal myoblasts, pancreatic parenchymal cells, pancreatic islet cells, pancreatic endocrine cells, pancreatic exocrine cells, pancreatic ductal cells, liver cells (e.g., hepatocytes), thyroid cells, parathyroid cells, adrenal cells, pituitary cells, splenic cells, pinealocytes, renal cells (nephrocytes), spleen cells, anterior pituitary cells, somatotropic cells, dopamine-producing cells, blood cells, cardiac muscle cells, skeletal muscle cells, osteoblasts, nerve cells, pigment cells, adipocytes, etc. These cells may be cells isolated from a living body or may be cells differentiated from stem cells as described later.

The stem cells (e.g., iPS cells) and other types of cells that can be induced to differentiate may be implanted as it is in a living body, or incorporated in the device and implanted in a living body and then induced to differentiate in the living body.

Alternatively, differentiated cells may be implanted in a living body or incorporated in the device.

The stem cells may be, but are not limited to, tissue-resident stem cells, such as epidermal stem cells, hair follicle stem cells, pancreatic stem cells, pancreatic progenitor cells, liver stem cells, neural stem cells, retinal stem cells, and hematopoietic stem cells; embryonic stem cells (ES cells); induced pluripotent stem cells (iPS cells); etc.

These cells are preferably from a mammal, such as a human, a monkey, a pig, a rat, a mouse, a dog, or cat, and are preferably capable of producing and/or secreting a physiologically active substance, such as a hormone or a protein useful for a living body, such as a patient. The type of cells to be implanted can be selected depending on the type of disease in the recipient, such as a patient, to undergo the implantation. When the cells are non-human cells, the cells may carry a human gene introduced thereinto for therapeutic purposes. Examples of the hormone useful for a living body include insulin, thyroid-stimulating hormone, thyroid hormones, parathyroid hormone, growth hormone, thyroxine, glucocorticoids, glucagon, estradiol, and testosterone. Specific examples of the protein useful for a living body include blood coagulation factors, complements, albumin, globulin, and various enzymes, such as metabolic enzymes or digestive enzymes, such as amylase, protease and lipase. Examples of other physiologically active substances include neurotransmitters, such as dopamine.

Specifically, the cells are more preferably pancreatic cells, in particular, pancreatic islet cells, hepatocytes, dopamine-producing cells, or stem cells or progenitor cells that give rise to these cells, and are further preferably pancreatic cells, in particular, pancreatic islet cells, or pancreatic progenitor cells or pancreatic stem cells. In an exemplary example, pancreatic islets or pancreatic cells, hepatocytes, stem/progenitor cells that give rise to these cells, etc. may be suitable for use.

The biological composition contained in the cell-containing device may be cells or living tissue established for laboratory use, or cells isolated from living tissue. The biological composition is preferably differentiated non-dividing cells. The isolation may be performed by any isolation method in accordance with a conventionally known method. The cells isolated from living tissue are desirably subjected to removal of pathogens, such as pathogenic viruses.

The amount of the biological composition contained in the cell-containing device may be adjusted as appropriate for the type of biological composition.

The dosage is determined by a physician considering the age, sex and symptoms of the patient, adverse side effects, and other factors, and is not limited to a specific amount. Typically, about one to ten devices may be implanted in an adult human. For example, a diabetic patient may receive the cell-containing device containing typically 1,000 to 1,000,000 IEQ/kg body weight islets, preferably 5,000 to 400,000 IEQ/kg body weight islets, and more preferably 10,000 to 20,000 IEQ/kg body weight islets (IEQ: international unit of the number of pancreatic islets; one IEQ is defined as the volume of a single islet of 150 μm in diameter).

The cell-embedding device is formed by embedding the biological composition in the device as described above. The cell-embedding device may be in any shape, and may be in a similar shape as that of the device 1, in particular, a similar shape as that of the non-bioabsorbable material contained in the device 1, and may, in particular, be in the same shape as that of the device 1, in particular, the same shape as that of the non-bioabsorbable material contained in the device 1. The cell-embedding device may thus be in the shape as exemplified above, including a disk, a sphere, a cylinder, an ellipsoid or other shapes, but is preferably in a disk shape.

The cell-embedding device, in particular, the device element thereof, may be made of any material, and may be made of a macromolecule (polymer), a metal, ceramics, etc.

The polymer used to produce the cell-embedding device is not limited to a particular polymer, and may be selected from, for example, structural proteins such as collagen, elastin and keratin; gelatin; glycosaminoglycans such as hyaluronic acid, chondroitin sulfate, keratan sulfate, dermatan sulfate, heparan sulfate and heparin; proteoglycans; cell adhesion molecules such as fibronectin, laminin, fibrinogen and vitronectin; fibrin; fibroin; sericin; alginic acid; chitosan; agarose; cellulose; cellulose derivatives such as cellulose nanofibers, carboxymethyl cellulose, and hydroxypropyl cellulose; synthetic polypeptides; polylactic acid; polyglycolic acid; polycaprolactone; polyethylene glycol; polypropylene glycol; 2-methacryloyloxyethyl phosphorylcholine; poly(meth)acrylic acid; polyacrylamide; poly-N-isopropylacrylamide; dextrin; silicone; polyurethane; fluororesins such as polytetrafluoroethylene and perfluoroalkoxyalkane; polyvinyl alcohol resins; and others.

The polymer may be a hydrophilic polymer or a water-soluble polymer. The hydrophilic polymer or the water-soluble polymer contained in the cell-embedding device may typically be converted into a water-insoluble form, e.g., a gel, by crosslinking or other techniques.

The polymer may be a single type or a combination of two or more types.

A polyvinyl alcohol resin is particularly preferred among the polymers as exemplified above. Accordingly, the polymer may contain at least a polyvinyl alcohol resin.

The polyvinyl alcohol resin will be described in detail below.

Polyvinyl Alcohol Resin

The polyvinyl alcohol resin may typically be a saponified product of a polymer containing at least a vinyl ester monomer as a polymerization component. Such a polyvinyl alcohol resin may be any polyvinyl alcohol resin containing vinyl alcohol units, and may contain vinyl ester units or structural units derived from a vinyl ester monomer, e.g., structural units derived from a fatty acid vinyl ester, such as vinyl acetate units and vinyl pivalate units (described later) and/or may contain other units, e.g., structural units derived from an unsaturated monomer having an active carbonyl group (described later) or other structural units derived from other unsaturated monomers.

The viscosity of a 4% by mass aqueous solution of the polyvinyl alcohol resin (at 20° C.) may be, for example, but is not limited to, 1 mPa·s or more, 2 mPa·s or more, 3 mPa·s or more, 5 mPa·s or more, 20 mPa·s or more, 30 mPa·s or more, 40 mPa·s or more, 50 mPa·s or more, etc., or may be, for example, 800 mPa·s or less, 500 mPa·s or less, 300 mPa·s or less, 200 mPa·s or less, 150 mPa·s or less, 100 mPa·s or less, 80 mPa·s or less, etc.

Typically, a polyvinyl alcohol resin having a viscosity of about 3 to 300 mPa·s as measured as a 4% by mass aqueous solution may be used as a suitable polyvinyl alcohol resin.

The viscosity of a 4% by mass aqueous solution of a polyvinyl alcohol resin may be measured in accordance with, for example, JIS K 6726.

The polyvinyl alcohol resin used in the invention can be selected in terms of its type, composition, etc., and may be, but is not limited to, a completely saponified polyvinyl alcohol resin (e.g., having a degree of saponification of 97 mol % or more), or a partially saponified polyvinyl alcohol resin (e.g., having a degree of saponification of less than 97 mol %).

The (average) degree of saponification may be measured in accordance with, for example, JIS K 6726.

In particular, a polyvinyl alcohol resin suitable as the polyvinyl alcohol resin (A) may be at least one selected from a modified polyvinyl alcohol resin having an active carbonyl group (A1), a polyvinyl alcohol resin having a triad syndiotacticity of 32 to 40% (A2), and a polyvinyl alcohol resin having a degree of saponification of 97 mol % or more (A3).

These resins (A1) to (A3) will be described in detail below.

Modified Polyvinyl Alcohol Resin Having Active Carbonyl Group

The modified polyvinyl alcohol resin having an active carbonyl group (simply called the modified PVA resin herein) may be, for example, a modified PVA copolymer produced by copolymerization of a fatty acid vinyl ester with an unsaturated monomer having an active carbonyl group followed by saponification of the resulting copolymer, or a post-modified PVA produced by directly contacting a conventionally produced PVA or modified PVA resin with a compound having an active carbonyl group, such as liquid diketene or diketene gas. A modified PVA copolymer is preferred for better stability and safety of the PVA resin and for better workability in the gelation process.

The fatty acid vinyl ester used in the production of the modified PVA copolymer may be, for example, but is not limited to, vinyl formate, vinyl acetate, vinyl propionate, vinyl pivalate, etc., and vinyl acetate is industrially preferred. These fatty acid vinyl esters may be subjected to a conventionally known polymerization method, such as bulk polymerization, solution polymerization, suspension polymerization, and emulsion polymerization. Solution polymerization using an alcoholic solvent, such as methanol, is industrially preferred.

The unsaturated monomer having an active carbonyl group may be, for example, but is not limited to, diacetone acrylamide, diacetone methacrylamide, diacetone acrylate, diacetone methacrylate, acetoacetoxy acrylamide, acetoacetoxy methacrylamide, etc. These unsaturated monomers may be used alone or in combination of two or more. Diacetone acrylamide is industrially preferred. The modified PVA copolymer is preferably diacetone acrylamide-modified PVA.

The copolymerization reaction between the fatty acid vinyl ester and the unsaturated monomer having an active carbonyl group according to the present invention may further include an additional unsaturated monomer capable of copolymerizing with the fatty acid vinyl ester and the unsaturated monomer having an active carbonyl group to the extent that the additional unsaturated monomer does not impair the effects of the invention.

The additional unsaturated monomer may be one or more unsaturated monomers selected from carboxyl group-containing unsaturated monomers, such as (meth)acrylic acid, maleic acid, maleic anhydride, fumaric acid, crotonic acid, itaconic acid, and undecylenic acid; unsaturated dibasic acid monoalkyl esters, such as monomethyl maleate and monomethyl itaconate; amide group-containing unsaturated monomers, such as acrylamide, dimethylacrylamide, dimethylaminoethylacrylamide, diethylacrylamide, dimethylaminopropylacrylamide, isopropylacrylamide, N-methylolacrylamide, and N-vinylacetamide; vinyl halides, such as vinyl chloride and vinyl fluoride; glycidyl group-containing unsaturated monomers, such as allyl glycidyl ether and glycidyl methacrylate; lactam group-containing unsaturated monomers including, e.g., N-vinylpyrrolidones such as N-vinyl-2-pyrrolidone and N-vinyl-alkylpyrrolidone (e.g., N-vinyl-mono- or di-$C_{1-4}$ alkyl-pyrrolidones, such as N-vinyl-3-propyl-2-pyrrolidone, N-vinyl-5-methyl-2-pyrrolidone, N-vinyl-5-ethyl-2-pyrrolidone, N-vinyl-5,5-dimethyl-2-pyrrolidone, and N-vinyl-3,5-dimethyl-2-pyrrolidone), N-allylpyrrolidones such as N-allyl-2-pyrrolidone, N-vinylpiperidones such as N-vinyl-2-piperidone and N-vinyl-alkylpiperidone (e.g., N-vinyl-mono- or di-$C_{1-4}$ alkyl-piperidones, such as N-vinyl-6-methyl-2-piperidone and N-vinyl-6-ethyl-2-piperidone), and N-vinylcaprolactams such as N-vinyl-ε-caprolactam and N-vinyl-alkylcaprolactam (e.g., N-vinyl-mono- or di-$C_{1-4}$ alkyl-caprolactams, such as N-vinyl-7-methyl-2-caprolactam and N-vinyl-7-ethyl-2-caprolactam); alkyl vinyl ethers such as $C_{1-20}$ alkyl vinyl ethers (e.g., methyl vinyl ether, n-propyl vinyl ether, i-propyl vinyl ether, n-butyl vinyl ether, i-butyl vinyl ether, t-butyl vinyl ether, lauryl vinyl ether, dodecyl vinyl ether, and stearyl vinyl ether); nitriles such as acrylonitrile and methacrylonitrile; hydroxy group-containing unsaturated monomers, including, e.g., $C_{1-20}$ monoalkyl allyl alcohols such as allyl alcohol and isopropenyl allyl alcohol, $C_{1-20}$ dialkyl allyl alcohols such as dimethyl allyl alcohol, and hydroxy $C_{1-20}$ alkyl vinyl ethers such as hydroxy ethyl vinyl ether and hydroxy butyl vinyl ether; acetyl group-containing unsaturated monomers, including, e.g., $C_{1-20}$ alkyl allyl acetates such as allyl acetate, dimethylallyl acetate, and isopropenylallyl acetate; (meth) acrylic acid esters, including, e.g., (meth)acrylic acid alkyl esters, such as (meth)acrylic acid $C_{1-20}$ alkyl esters such as methyl (meth)acrylate, ethyl (meth)acrylate, 2-ethylhexyl acrylate, and n-butyl acrylate; vinylsilanes such as trimethoxyvinyl silane, tributylvinyl silane, and diphenylmethylvinylsilane; polyoxyalkylene (meth)acrylates, such as polyoxyethylene (m eth)acrylate and polyoxypropylene (meth)acrylate; polyoxyalkylene (meth)acrylamides, such as polyoxyethylene (meth)acrylamide and polyoxypropylene (meth)acrylamide; polyoxyalkylene vinyl ethers, such as polyoxyethylene vinyl ether and polyoxypropylene vinyl ether; polyoxyalkylene alkylvinyl ethers, such as polyoxyethylene allyl ether, polyoxypropylene allyl ether, polyoxyethylene butylvinyl ether, and polyoxypropylene butylvinyl ether; α-olefins such as ethylene, propylene, n-butene, and 1-hexene; butenes such as 3,4-dihydroxy-1-butene, 3,4-diacyloxy-1-butene, 3-acyloxy-4-hydroxy-1-butene, 4-acyloxy-3-hydroxy-1-butene, and 3,4-diacyloxy-2-methyl-1-butene; pentenes such as 4,5-dihydroxy-1-pentene, 4,5-diacyloxy-1-pentene, 4,5-dihydroxy-3-methyl-1-pentene, and 4,5-diacyloxy-3-methyl-1-pentene; hexenes such as 5,6-dihydroxy-1-hexene and 5,6-diacyloxy-1-hexene; unsaturated amine monomers, such as N,N-dimethylallylamine, N-allylpiperazine, 3-piperidine acrylic acid ethyl ester, 2-vinylpyridine, 4-vinylpyridine, 2-methyl-6-vinylpyridine, 5-ethyl-2-vinylpyridine, 5-butenylpyridine, 4-pentenylpyridine, and 2-(4-pyridyl)allyl alcohol; quaternary ammonium compound-containing unsaturated monomers, such as dimethylaminoethyl acrylate methyl chloride quaternary salt, N,N-dimethylaminopropyl acrylamide methyl chloride quaternary salt, and N,N-dimethylaminopropyl acrylamide methyl benzenesulfonate quaternary salt; aromatic unsaturated monomers such as styrene; sulfonic acid group-containing unsaturated monomers, such as 2-acrylamide-2-methylpropanesulfonic acid or its alkali metal salts, ammonium salts or organic amine salts, 2-acrylamide-1-methylpropanesulfonic acid or its alkali metal salts, ammonium salts or organic amine salts, 2-methacrylamide-2- methylpropanesulfonic acid or its alkali metal salts, ammonium salts or organic amine salts, vinyl sulfonic acid or its alkali metal salts, ammonium salts or organic amine salts, allyl sulfonic acid or its alkali metal salts, ammonium salts or organic amine salts, and methallyl sulfonic acid or its alkali metal salts, ammonium salts or organic amine salts; glycerol monoallyl ether; 2,3-diacetoxy-1-allyloxypropane; 2-acetoxy-1-allyloxy-3-hydroxypropane; 3-acetoxy-1-allyloxy-3-hydroxypropane; 3-acetoxy-1-allyloxy-2-hydroxy-propane; glycerol monovinyl ether; glycerol monoisopropenyl ether; acryloyl morpholine; vinyl ethylene carbonate; vinylimidazole; and vinylcarbazole.

The amount of the additional unsaturated monomer may be, for example, but is not limited to, 10 mol or less relative to 100 mol of the vinyl ester monomers.

The produced modified PVA copolymer may be post-modified by acetalization, urethanation, etherification, grafting, phosphorylation, acetoacetylation, cationization, or other reactions in accordance with a known method to the extent that the effects of the present invention are not impaired.

A polymerization catalyst is used in the production of the modified PVA copolymer, and may typically be, but is not limited to, an azo compound or a peroxide.

An organic acid, such as tartaric acid, citric acid, and acetic acid, may be added to the polymerization reaction to prevent the hydrolysis of the fatty acid vinyl ester.

A polymerization terminator may be used to terminate the polymerization. The polymerization terminator may be, for example, but is not limited to, m-dinitrobenzene etc.

The shape of a polymerization vessel, the type of a polymerization agitator, the polymerization temperature, the pressure in the polymerization vessel, or other conditions in the copolymerization of the fatty acid vinyl ester and the unsaturated monomer having an active carbonyl group according to the present invention may be in accordance with a conventionally known method.

The copolymer of the fatty acid vinyl ester and the unsaturated monomer having an active carbonyl group may be saponified by any conventionally known method according to the present invention. For example, a conventionally known alcoholysis or hydrolysis is applicable using a basic catalyst, such as sodium hydroxide, potassium hydroxide or sodium methoxide, or an acidic catalyst, such as hydrochloric acid, sulfuric acid or p-toluene sulfonic acid.

The solvent used in the saponification reaction may be, for example, an alcohol such as methanol or ethanol; an ester such as methyl acetate; a ketone such as acetone or methyl ethyl ketone; an aromatic hydrocarbon such as benzene or toluene; tetrahydrofuran; etc. These solvents may be used alone or in combination of two or more. The temperature, duration, and other conditions of the saponification reaction are not particularly limited.

The drying, grinding or washing of the saponified product may be done by any methods and may be performed by a conventionally known method.

When the modified PVA resin is a PVA modified with the unsaturated monomer having an active carbonyl group (e.g., diacetone acrylamide), the amount of the unsaturated monomer units having an active carbonyl group (e.g., diacetone acrylamide units) contained in the modified PVA resin is, for example, 0.5 to 20 mol %, preferably 0.5 to 15 mol %, more preferably 1 to 12 mol %, and further preferably 2 to 10 mol % (e.g., 3 to 8 mol %) relative to the all the structural units in the modified PVA resin (relative to the total amount of the structural monomers).

The amount of the unsaturated monomer units having an active carbonyl group (e.g., diacetone acrylamide units) contained in the modified PVA resin is preferably 0.5 mol % or more, and the modified PVA resin containing such an amount of the unsaturated monomer units may have many reactive sites with a crosslinking agent and have sufficient strength (stress) as a cell-embedding device. The amount of the unsaturated monomer units contained in the modified PVA resin is preferably 20 mol % or less, and the modified PVA resin containing such an amount of the unsaturated monomer units may have improved solubility in water.

The degree of saponification of the modified PVA resin is preferably, but not limited to, 80 mol % or more (e.g., 80 to 99.9 mol %), more preferably 88 mol % or more (e.g., 88 to 99.9 mol %), and further preferably 95 mol % or more (e.g., 95 to 99.9 mol %).

The viscosity of the modified PVA resin may vary. A 4 mass % aqueous solution of the modified PVA resin (at 20° C.) may have a viscosity of preferably 2 to 500 mPa·s, more preferably 3 to 300 mPa·s, and further preferably 5 to 200 mPa·s, e.g., 5 to 80 mPa·s, and may have a viscosity of typically 500 mPa·s or less, e.g., 20 to 500 mPa·s, 30 to 500 mPa·s, to 500 mPa·s, 50 to 500 mPa·s, etc.; 300 mPa·s or less, e.g., 20 to 300 mPa·s, 30 to 300 mPa·s, 40 to 300 mPa·s, 50 to 300 mPa·s; 200 mPa·s or less, e.g., 20 to 200 mPa·s, 30 to 200 mPa·s, 40 to 200 mPa·s, 50 to 200 mPa·s; etc.

The degree of saponification and the viscosity of a 4 mass % aqueous solution may be measured in accordance with JIS K 6726.

Polyvinyl Alcohol Resin Having Triad Syndiotacticity of 32 to 40%

The polyvinyl alcohol resin may preferably be a polyvinyl alcohol resin having a triad syndiotacticity of 32 to 40% (simply also called the highly syndiotactic PVA resin herein).

The highly syndiotactic PVA resin preferably has a triad syndiotacticity of 32 to 40%, more preferably 33 to 39%, and further preferably 34 to 38%. The highly syndiotactic PVA resin having a triad syndiotacticity of 32% or more easily forms an aqueous gel, and the highly syndiotactic PVA resin having a triad syndiotacticity of 40% or less can easily form an aqueous gel.

The triad syndiotacticity can be determined from the peaks attributed to hydroxy groups in the proton NMR analysis of the highly syndiotactic PVA resin dissolved in deuterated dimethylsulfoxide (DMSO).

The highly syndiotactic PVA resin may be produced by any method that yields the highly syndiotactic PVA resin having a triad syndiotacticity of 32 to 40%. The highly syndiotactic PVA resin can easily be produced by saponifying a vinyl ester polymer prepared by a conventionally known method.

That is, the highly syndiotactic PVA resin is a saponified product of a vinyl ester polymer.

The vinyl ester polymer may be produced by any method that includes polymerization of vinyl ester monomers, and may be performed in accordance with a conventionally known method.

The shape of a polymerization vessel, the type of a polymerization agitator, the polymerization temperature, the pressure in the polymerization vessel, or other conditions may also be in accordance with a conventionally known method. The polymerization method may be selected from various conventionally known methods, including bulk polymerization, solution polymerization, suspension polymerization, emulsion polymerization, or other polymerization methods. For ease of controlling the degree of polymerization or performing a saponification reaction after polymerization, preferred polymerization methods are, but not limited to, solution polymerization using an alcohol as a solvent, or suspension polymerization using water or a combination of water and an alcohol as a dispersion medium.

Examples of the vinyl ester monomers include vinyl esters, such as fatty acid vinyl esters and non-fatty acid vinyl esters, e.g., vinyl formate, aromatic carboxylic acid vinyl esters, etc. For production of a PVA having a high syndiotacticity, the vinyl ester monomers may be $C_{3-15}$ fatty acid vinyl esters, e.g., linear or branched $C_{3-15}$ fatty acid vinyl esters, such as vinyl propionate, vinyl butyrate, and vinyl pivalate, and preferably $C_{3-10}$ fatty acid vinyl esters, such as linear or branched $C_{3-10}$ fatty acid vinyl esters; $C_{3-15}$ fatty acid vinyl esters having one or more substituents (e.g., a halogen group), such as vinyl trifluoroacetate and vinyl trichloroacetate; vinyl formate; etc. These vinyl esters can be used alone or in combination of two or more.

Specific examples of the method for producing the highly syndiotactic PVA include a method including homopolymerization or copolymerization of vinyl ester monomers having a bulky side chain, such as vinyl propionate, vinyl butyrate, and vinyl pivalate, followed by saponification of the product using an alkaline catalyst; and a method including homopolymerization or copolymerization of vinyl ester monomers having a high polarity, such as vinyl formate, vinyl trifluoroacetate, and vinyl trichloroacetate, followed by saponification of the product using an alkaline catalyst. Preferred methods include polymerization of vinyl pivalate followed by saponification of the product using an alkaline catalyst. An example of a production process of a PVA resin having a triad syndiotacticity of 37.1% will be described in Examples later. The triad syndiotacticity of the PVA resin can be reduced to less than 37.1% by, for example, adding vinyl acetate to the polymerization reaction of vinyl pivalate to give a vinyl pivalate-vinyl acetate copolymer, or by raising the polymerization temperature. The triad syndiotacticity of the PVA resin can be increased to more than 37.1% by, for example, lowering the polymerization temperature in the example of the production process. In any case, the triad syndiotacticity of the resulting highly syndiotactic PVA can be determined from the peaks attributed to hydroxy groups in the proton NMR analysis of the highly syndiotactic PVA resin dissolved in deuterated DMSO. The highly syndiotactic PVA resin determined to have a triad syndiotacticity of 32 to 40% can be selected as appropriate and used in the present invention.

The vinyl ester polymer containing the above vinyl ester monomers may further contain an additional unsaturated monomer capable of copolymerizing with the vinyl ester monomers to the extent that the additional unsaturated monomer does not impair the effects of the invention.

The additional unsaturated monomer may be one or more unsaturated monomers selected from carboxyl group-containing unsaturated monomers, such as (meth)acrylic acid, maleic acid, maleic anhydride, fumaric acid, crotonic acid, itaconic acid, and undecylenic acid; unsaturated dibasic acid monoalkyl esters, such as monomethyl maleate and monomethyl itaconate; amide group-containing unsaturated monomers, such as acrylamide, dimethylacrylamide, dimethylaminoethylacrylamide, diethylacrylamide, dimethylaminopropylacrylamide, isopropylacrylamide, N-methylolacrylamide, and N-vinylacetamide; vinyl halides, such as vinyl chloride and vinyl fluoride; glycidyl group-containing unsaturated monomers, such as allyl glycidyl ether and glycidyl methacrylate; lactam group-containing unsaturated monomers including, e.g., N-vinylpyrrolidones such as N-vinyl-2-pyrrolidone and N-vinyl-alkylpyrrolidone (e.g., N-vinyl-mono- or di-$C_{1-4}$ alkyl-pyrrolidones, such as N-vinyl-3-propyl-2-pyrrolidone, N-vinyl-5-methyl-2-pyrrolidone, N-vinyl-5-ethyl-2-pyrrolidone, N-vinyl-5,5-dimethyl-2-pyrrolidone, and N-vinyl-3,5-dimethyl-2-pyrrolidone), N-allylpyrrolidones such as N-allyl-2-pyrrolidone, N-vinylpiperidones such as N-vinyl-2-piperidone and N-vinyl-alkylpiperidone (e.g., N-vinyl-mono- or di-$C_{1-4}$ alkyl-piperidones, such as N-vinyl-6-methyl-2-piperidone and N-vinyl-6-ethyl-2-piperidone), and N-vinylcaprolactams such as N-vinyl-ε-caprolactam and N-vinyl-alkylcaprolactam (e.g., N-vinyl-mono- or di-$C_{1-4}$ alkyl-caprolactams, such as N-vinyl-7-methyl-2-caprolactam and N-vinyl-7-ethyl-2-caprolactam); alkyl vinyl ethers such as $C_{1-20}$ alkyl vinyl ethers (e.g., methyl vinyl ether, n-propyl vinyl ether, i-propyl vinyl ether, n-butyl vinyl ether, i-butyl vinyl ether, t-butyl vinyl ether, lauryl vinyl ether, dodecyl vinyl ether, and stearyl vinyl ether); nitriles such as acrylonitrile and methacrylonitrile; hydroxy group-containing unsaturated monomers, including, e.g., $C_{1-20}$ monoalkyl allyl alcohols such as allyl alcohol and isopropenyl allyl alcohol, $C_{1-20}$ dialkyl allyl alcohols such as dimethyl allyl alcohol, and hydroxy $C_{1-20}$ alkyl vinyl ethers such as hydroxy ethyl vinyl ether and hydroxy butyl vinyl ether; acetyl group-containing unsaturated monomers, including, e.g., $C_{1-20}$ alkyl allyl acetates such as allyl acetate, dimethylallyl acetate, and isopropenylallyl acetate; (meth) acrylic acid esters, including, e.g., (meth)acrylic acid alkyl esters, such as (meth)acrylic acid $C_{1-20}$ alkyl esters such as methyl (meth)acrylate, ethyl (meth)acrylate, 2-ethylhexyl acrylate, and n-butyl acrylate; vinylsilanes such as trimethoxyvinyl silane, tributylvinyl silane, and diphenylmethylvinylsilane; polyoxyalkylene (meth)acrylates, such as polyoxyethylene (meth)acrylate and polyoxypropylene (meth)acrylate; polyoxyalkylene (meth)acrylamides, such as polyoxyethylene (meth)acrylamide and polyoxypropylene (meth)acrylamide; polyoxyalkylene vinyl ethers, such as polyoxyethylene vinyl ether and polyoxypropylene vinyl ether; polyoxyalkylene alkylvinyl ethers, such as polyoxyethylene allyl ether, polyoxypropylene allyl ether, polyoxyethylene butylvinyl ether, and polyoxypropylene butylvinyl ether; α-olefins such as ethylene, propylene, n-butene, and 1-hexene; butenes such as 3,4-dihydroxy-1-butene, 3,4-diacyloxy-1-butene, 3-acyloxy-4-hydroxy-1-butene, 4-acyloxy-3-hydroxy-1-butene, and 3,4-diacyloxy-2-methyl-1-butene; pentenes such as 4,5-dihydroxy-1-pentene, 4,5-diacyloxy-1-pentene, 4,5-dihydroxy-3-methyl-1-pentene, and 4,5-diacyloxy-3-methyl-1-pentene; hexenes such as 5,6-dihydroxy-1-hexene and 5,6-diacyloxy-1-hexene; unsaturated amine monomers, such as N,N-dimethylallylamine, N-allylpiperazine, 3-piperidine acrylic acid ethyl ester, 2-vinylpyridine, 4-vinylpyridine, 2-methyl-6-vinylpyridine, 5-ethyl-2-vinylpyridine, 5-butenylpyridine, 4-pentenylpyridine, and 2-(4-pyridyl)allyl alcohol; quaternary ammonium compound-containing unsaturated monomers, such as dimethylaminoethyl acrylate methyl chloride quaternary salt, N,N-dimethylaminopropyl acrylamide methyl chloride quaternary salt, and N,N-dimethylaminopropyl acrylamide methyl benzenesulfonate quaternary salt; aromatic unsaturated monomers such as styrene; sulfonic acid group-containing unsaturated monomers, such as 2-acrylamide-2-methylpropanesulfonic acid or its alkali metal salts, ammonium salts or organic amine salts, 2-acrylamide-1-methylpropanesulfonic acid or its alkali metal salts, ammonium salts or organic amine salts, 2-methacrylamide-2-methylpropanesulfonic acid or its alkali metal salts, ammonium salts or organic amine salts, vinyl sulfonic acid or its alkali metal salts, ammonium salts or organic amine salts, allyl sulfonic acid or its alkali metal salts, ammonium salts or organic amine salts, and methallyl sulfonic acid or its alkali metal salts, ammonium salts or organic amine salts; glycerol monoallyl ether; 2,3-diacetoxy-1-allyloxypropane; 2-acetoxy-1-allyloxy-3-hydroxypropane; 3-acetoxy-1-allyloxy-3-hydroxypropane; 3-acetoxy-1-allyloxy-2-hydroxypropane; glycerol monovinyl ether; glycerol monoisopropenyl ether; acryloyl morpholine; vinyl ethylene carbonate; vinylimidazole; and vinylcarbazole.

The amount of the additional unsaturated monomer may be, for example, but is not limited to, 10 mol or less relative to 100 mol of the vinyl ester monomers.

A polymerization catalyst may be used for the polymerization. The polymerization catalyst may typically be, but is not limited to, an azo compound or a peroxide.

An organic acid, such as tartaric acid, citric acid, and acetic acid, may be added to the polymerization reaction to prevent the hydrolysis of the fatty acid vinyl ester.

A polymerization terminator may be used to terminate the polymerization. The polymerization terminator may be, for example, but is not limited to, m-dinitrobenzene etc.

The polymerization temperature may be set at any temperature known to be used in polymerization. For ease of production of a PVA resin having a high syndiotacticity and other reasons, the polymerization temperature is, for example, −50 to 200° C., preferably −50 to 150° C., and more preferably 0 to 120° C.

The vinyl ester polymer is produced in the manner as described above. The resulting polymer may be saponified by any conventionally known method. For example, a conventionally known alcoholysis or hydrolysis is applicable using a basic catalyst, such as sodium hydroxide, potassium hydroxide or sodium methoxide, or an acidic catalyst, such as hydrochloric acid, sulfuric acid or p-toluenesulfonic acid. The syndiotacticity of the polymer is usually not greatly changed before and after the saponification reaction.

The solvent used in the saponification may be, for example, an alcohol such as methanol or ethanol; an ester such as methyl acetate or ethyl acetate; a ketone such as acetone or methyl ethyl ketone; an aromatic hydrocarbon such as benzene or toluene; tetrahydrofuran; etc. These solvents may be used alone or in combination of two or more. The temperature, duration, and other conditions of the saponification are not particularly limited.

The drying, grinding or washing of the saponified product may be done by any methods and may be performed by a conventionally known method.

A saponified product of the vinyl ester polymer, i.e., the highly syndiotactic PVA resin according to the present invention is produced in the manner as described above.

The produced highly syndiotactic PVA resin may be post-modified by acetalization, urethanation, etherification, grafting, phosphorylation, acetoacetylation, cationization, or other reactions following a known method to the extent that the effects of the present invention are not impaired.

The degree of saponification of the highly syndiotactic PVA resin is preferably 90 to 99.9 mol %, more preferably 98 to 99.9 mol %, and further preferably 99 to 99.9 mol %. The degree of saponification of the highly syndiotactic PVA resin can be determined by, for example, proton NMR analysis in a deuterated DMSO solution.

The degree of polymerization of the highly syndiotactic PVA resin is preferably 100 to 10,000, more preferably 500 to 8,000, and further preferably 1,000 to 5,000. For ease of handling, the degree of polymerization is particular preferably 1,000 to 3,000. The highly syndiotactic PVA resin having a degree of polymerization of 100 or more can be used to easily produce an aqueous gel having a high resin strength (stress) and shape retainability. When the degree of polymerization is 10,000 or less, an aqueous solution of the resin can easily be handled. The degree of polymerization is measured before saponification and is determined in terms of the degree of polymerization of polyvinyl acetate in a benzene solution at 30° C. in accordance with JIS K 6725.
Polyvinyl Alcohol Resin Having Degree of Saponification of 97 Mol % or More The polyvinyl alcohol resin may be a polyvinyl alcohol resin having a degree of saponification of 97 mol % or more (simply also called the completely saponified PVA resin herein) as described above.

The degree of saponification of the completely saponified PVA resin is preferably 97 mol % or more, e.g., 97 to 99.9 mol %, more preferably 98 mol % or more, e.g., 98 to 99.9 mol %, and particularly preferably 98.5 mol % or more, e.g., 98.5 to 99.9 mol %.

The degree of polymerization of the completely saponified PVA resin is, for example, 100 to 10,000, more preferably 500 to 9,000, further preferably 1,000 to 8,000, and particularly preferably 1,500 to 5,000.
Crosslinking Agent The cell-embedding device or the polymer that constitutes the cell-embedding device may further comprise a crosslinking agent.

The crosslinking agent may be any crosslinking agent and may be selected depending on the type of polymer or other factors. For example, when the modified PVA resin is used as the polymer to produce the device, a suitable crosslinking agent may be a crosslinking agent having a functional group (e.g., a hydrazino group etc.) capable of reacting with the carbonyl groups of the modified PVA resin.

Examples of the crosslinking agent include hydrazide compounds, semicarbazide compounds, or the like. Particularly preferred are hydrazide compounds, semicarbazide compounds, or the like having two or more functional groups selected from the groups represented by the formulas (1) to (3) below in the molecule. These compounds can be used alone or in combination of two or more.

$$-NH-NH_2 \tag{1}$$

$$-CO-NH-NH_2 \tag{2}$$

$$-NH-CO-NH-NH_2 \tag{3}$$

Specific examples of the hydrazide compounds include carbohydrazide; dicarboxylic acid hydrazides, including aliphatic dicarboxylic acid hydrazides, such as oxalic acid dihydrazide, malonic acid dihydrazide, succinic acid dihydrazide, glutaric acid dihydrazide, adipic acid dihydrazide, pimelic acid dihydrazide, suberic acid dihydrazide, azelaic acid dihydrazide, sebacic acid dihydrazide, dodecanedioic acid dihydrazide, and hexadecanedioic acid dihydrazide; aromatic dicarboxylic acid hydrazides, such as terephthalic acid dihydrazide, isophthalic acid dihydrazide, 2,6-naphthoic acid dihydrazide, and 4,4'-bisbenzene dihydrazide; alicyclic dicarboxylic acid hydrazides, such as 1,4-cyclohexanedicarboxylic acid dihydrazide; hydroxyl group-containing dicarboxylic dihydrazides, such as tartaric acid dihydrazide and malic acid dihydrazide; iminodiacetic acid dihydrazide; itaconic acid dihydrazide; 1,3-bis(hydrazinocarbonoethyl)-5-isopropylhydantoin; 7,11-octadecadiene-1,18-di carbohydrazide; tris(2-hydrazinocarbonylethyl)isocyanurate; citric acid trihydrazide; butanetricarbohydrazide; 1,2,3-benzenetrihydrazide; ethylenediaminetetraacetic acid tetrahydrazide; 1,4,5,8-naphthoic acid tetrahydrazide; nitriloacetic acid trihydrazide; cyclohexanetricarboxylic acid trihydrazide; pyromellitic acid tetrahydrazide; etc.

Examples of the semicarbazide compounds include N,N'-hexamethylene bissemicarbazide, and biuretry-tri(hexamethylenesemicarbazide).

Derivatives produced by a reaction of these hydrazide compounds or semicarbazide compounds with low boiling point ketones, such as acetone and methyl ethyl ketone, may also be used.

Dicarboxylic acid hydrazides, polyacrylic acid hydrazide and the like are preferred, adipic acid dihydrazide, polyacrylic acid hydrazide and the like are more preferred, and polyacrylic acid hydrazide is particularly preferred among the crosslinking agents as exemplified above. These crosslinking agents are suitable for the invention due to low toxicity, high solubility in water, and other advantages.

The crosslinking agents as described above may be used alone or in combination of two or more.

The amount of the crosslinking agent(s) contained in the polymer is preferably 1 to parts by mass, more preferably 2 to 25 parts by mass, and further preferably 3 to 20 parts by mass, e.g., 4 to 15 parts by mass, relative to 100 parts by mass of the polymer (e.g., the modified PVA resin).

The amount of the crosslinking agent(s) is 1 part by mass or more such that high crosslinking density and sufficient strength (stress) as the cell-embedding device are achieved. The amount of the crosslinking agent(s) is 30 parts by mass or less such that residual unreacted crosslinking agent(s) can be minimized.

When the crosslinking agent is polyacrylic acid hydrazide, the weight average molecular weight (Mw) of the polyacrylic acid hydrazide is preferably, but not limited to, about 3,000 to 6,000,000, more preferably about 5,000 to 1,000,000, and further preferably about 8,000 to 800,000, e.g., about 10,000 to 300,000, about 1,000 to 200,000, or about 10,000 to 100,000.

When the crosslinking agent is polyacrylic acid hydrazide, the degree of hydrazidation of the polyacrylic acid hydrazide is preferably, but not limited to, 30% or more, more preferably 50% or more, further preferably 70% or more, and particularly preferably 80% or more.

The molecular weight and the degree of hydrazidation of polyacrylic acid hydrazide may be adjusted as appropriate to the extent that the effects of the present invention are not impaired. For example, when the molecular weight of polyacrylic acid hydrazide is small, the degree of hydrazidation is adjusted to be large. When the molecular weight of polyacrylic acid hydrazide is large, the degree of hydrazidation is adjusted to be small.

The polyvinyl alcohol resin contained in the cell-embedding device may be in the form of a gel, in particular, an aqueous gel (hydrogel), or a sponge.

The formation of the gel may be performed as appropriate for the type of polymer. For example, the gel may be formed by crosslinking the polymer with a crosslinking agent described later or other agents (gel crosslinking), or a polymer capable of forming a gel (e.g., the highly syndiotactic PVA resin as described above) may be used to form a gel.

The concentration of the polymer in the gel may be, for example, 0.3 to 20%, and is preferably 0.5 to 10%, more preferably 1 to 8%, for example, 3 to 8%. The gel containing such an amount of the polymer is preferred because the gel is capable of maintaining the shape of the encapsulating membrane-forming device implanted in the body of an animal for a long period of time and has other advantages.

When a crosslinking agent is used to form a gel, the amount of the crosslinking agent can be selected as appropriate for the type of crosslinking agent, the desired strength of the gel or other factors. The amount of the crosslinking agent may be, for example, 0.5 parts by mass or more, preferably 1 part by mass or more, more preferably 3 parts by mass or more, etc. relative to 100 parts by mass of the polymer. The amount of the crosslinking agent may be, for example, 20 parts by mass or less, preferably 18 parts by mass or less, more preferably 15 parts by mass or less, etc. relative to 100 parts by mass of the polymer.

When the polyvinyl alcohol resin is formed into a gel, the gel may be shaped or formed into a desired shape by, for example, a method involving pouring a liquid mixture (in particular, an aqueous solution that may be in a sol state) containing a polymer, e.g., the polyvinyl alcohol resin and optionally a crosslinking agent as needed, into a mold of the desired shape to form a gel; or a method involving cutting a produced gel with a knife etc. into the desired shape.

A liquid mixture (in particular, an aqueous solution) containing a polymer, e.g., the polyvinyl alcohol resin and optionally a crosslinking agent as needed typically undergoes a sol state to become a gel. Such a sol is understood to be an equivalent of the gel according to the present invention and is within the scope of the present invention.

The solid content of the liquid mixture (in particular, an aqueous solution that may be in a sol state) is, for example, 0.3 to 20% by mass, preferably 0.5 to 10% by mass, and more preferably 1 to 8% by mass. A gel prepared from the liquid mixture with such a solid content is preferred because the gel is capable of maintaining the shape of the device implanted in the body for a long period of time and retaining an adhesion preventive ability and has other advantages.

The aqueous solution containing the polyvinyl alcohol resin may be prepared in any manner, and may be prepared by a conventionally known method for dissolving a PVA, involving, e.g., dispersing the polyvinyl alcohol resin in water at room temperature, agitating the dispersion while raising the temperature to 80° C. or more to allow complete dissolution, and cooling the solution.

The crosslinking agent may be in the form of an aqueous solution. The aqueous solution of the crosslinking agent may be prepared in any manner, and may be prepared by, e.g., a method involving dispersing the crosslinking agent in water at room temperature, and agitating the dispersion at room temperature to allow dissolution.

Alternatively, the aqueous solution of the crosslinking agent may be prepared by a method involving dispersing the crosslinking agent in water at room temperature, agitating the dispersion under heating (e.g., at 60° C. for 10 minutes) to allow dissolution, and leaving the solution to stand at room temperature.

The aqueous solution of the polyvinyl alcohol resin and the aqueous solution of the crosslinking agent are desirably sterilized by a conventionally known method, such as autoclaving, UV, γ-rays or filtering. The addition of the biological composition under mixing and the subsequent production process of the cell-embedding device are desirably performed under germ-free conditions. The mixture and the cell-embedding device are desirably stored under germ-free conditions.

When the polyvinyl alcohol resin is formed into a sponge, a suitable method for forming a sponge may be, for example, a method involving adding a pore-forming agent in the production process of the gel, or a method involving drying, e.g., lyophilizing, a produced gel to form pores.

The pore-forming agent may be a water-soluble polymer, a water-soluble inorganic substance, an organic solvent, etc. A suitable pore-forming agent is starch.

When starch is used as a pore-forming agent, a crosslinking agent (e.g., formalin) is added to an aqueous solution containing the polyvinyl alcohol resin and starch, then the polyvinyl alcohol resin is gelled, and the starch is washed away with water to give a sponge.

When a pore-forming agent is used to form a sponge, the resulting sponge may be dried.

The cell-containing device may further contain a cell culture component.

The cell culture component may be, for example, but is not limited to, an alkali metal, an alkaline earth metal, a halogen, glucose, etc. Suitable cell culture components are an acetate buffer solution or a phosphate buffer solution containing Na, K, Cl, Ca, glucose and others.

When the cell culture component contains Na, the concentration of Na may be adjusted to preferably 20 to 150 mEq/L, more preferably 80 to 140 mEq/L.

When the cell culture component contains K, the concentration of K may be adjusted to preferably 2.5 to 130 mEq/L, more preferably 3.5 to 40 mEq/L.

When the cell culture component contains Cl, the concentration of Cl may be adjusted to preferably 15 to 170 mEq/L, more preferably 100 to 150 mEq/L. When the cell culture component contains Ca, the concentration of Ca may be adjusted to preferably 0.5 to 5 mEq/L, more preferably 1 to 3 mEq/L.

When the cell culture component contains glucose, the concentration of glucose may be adjusted to preferably 1 to 11 mM, more preferably 3 to 7 mM. The cell culture component may also be, for example, a known cell culture medium, such as Hanks' balanced salt solution (HB SS); a commercially available preservation solution, such as Euro-Collins solution, CELLBANKER, and UW solution (University of Wisconsin solution); a cell protective component, such as dimethylsulfoxide (DMSO) and serum albumin; a component for preventing the contamination by germs, such as antibiotics; a component for maintaining the activity of cells, such as vitamins such as nicotinamide; etc. The cell culture component is preferably a known cell culture medium etc.

These cell culture components can be used alone or in combination of two or more.

Such a cell culture component may be used in combination with another component, such as a sustained release agent, an isotonic agent, and a pH adjusting agent.

The cell-containing device may further contain a component other than those described above. The cell-containing device may further contain, for example, a growth factor (a cell growth factor), a cytokine, other physiologically active substances, a blood-flow accelerator, a neurotrophic factor, etc.

These components can be used alone or in combination of two or more.

Examples of the growth factor (cell growth factor) include the growth factors etc. as exemplified above, such as epidermal growth factor (EGF), hepatocyte growth factor (HGF) and insulin.

Examples of the cytokine include hematopoietic factors, such as interleukins, chemokines and colony-stimulating factors, tumor necrosis factors, and interferons.

Examples of other physiologically active substances include amino acids, such as glycine, phenylalanine, lysine, aspartic acid, and glutamic acid; vitamins, such as biotin, pantothenic acid, and vitamin D; serum albumin; and antibiotics.

Examples of the blood-flow accelerator include citrulline or salts thereof, capsaicin, and capsaicinoids.

Examples of the neurotrophic factor include nerve growth factor (NGF), brain-derived neurotrophic factor (BDNF), neurotrophin-3 (NT-3), neurotrophin-4 (NT-4), glial cell-derived neurotrophic factor (GDNF), neurturin, artemin, and persephin.

The amount of these components added to the cell-containing device is not limited to a particular amount.

The cell-containing device or the cell-embedding device may form a gel.

The gel typically has a predetermined strength (stress). The gel may sustain a sufficient stress not to easily break when the device is implanted. The strength of the gel may vary depending on the type of polymer (e.g., the type of polyvinyl alcohol resin, the viscosity of a 4% aqueous solution of the resin, the degree of saponification, the degree of modification, syndiotacticity, etc.), the type of crosslinking agent, the amount of the crosslinking agent added, the solid content of the gel, etc. The strength of the gel is therefore not limited to a specific value, but the gel may be able to sustain a stress of, for example, 0.5 to 100 kPa, preferably 0.6 to 95 kPa, more preferably 0.7 to 90 kPa, and further preferably 0.7 to 85 kPa, as measured at 20° C.

The stress sustained by the gel can be measured using, for example, a compact tabletop-tester EZ Test EZ-SX (Shimadzu Corporation) following the manufacturer's instructions.

The gel, in particular the aqueous gel, may be in any shape, and may be in the shape of, for example, not limited to, a sheet, a plate, a disk, a bar, a tube, a bead, etc.

The size of the gel, in particular the aqueous gel, may be selected as appropriate for the implantation site of the device and its size, etc., and is not particularly limited. For example, the thickness of the gel is preferably 0.1 to 10 mm, more preferably 0.2 to 5 mm, further preferably 0.5 to 2 mm, and particularly preferably 0.7 to 1.5 mm.

The cell-containing device may further contain a supporting substrate.

In particular, the gel, for example, the gel that forms a scaffold, may contain a supporting substrate useful as a reinforcement for the purpose of reinforcing the gel and/or for ease of handling.

For example, when the gel (in particular, in the form of an aqueous gel) is formed into a thin film, a polymer is placed on a substrate (a reinforcement), such as a mesh sheet made of a resin, for reinforcement and/or for ease of handling, and is then formed into a gel.

The material of the supporting substrate may be, but is not limited to, a polymer such as PET (polyethylene terephthalate), PE (polyethylene), PP (polypropylene), and Teflon (registered trademark); a metal; etc. The material of the supporting substrate preferably does not degrade or deteriorate in a living body, but may be a biodegradable material that degrades in a living body after a certain period of time has passed.

The mesh size of the mesh sheet is such a size that allows permeation of molecules that should be permeated through the mesh sheet and have an assumed maximum diameter of about 5 nm, such as oxygen, inorganic or organic nutrients and various hormones (e.g., physiologically active substances including hormones, such as insulin) while preventing permeation of molecules that should be prevented from permeating through the mesh sheet and have an assumed minimum diameter of about 50 nm, such as immune-related cells and immune-related substances (e.g., antibodies, complements, etc.). The mesh size of the mesh sheet is typically 5 to 100 nm, preferably 10 to 50 nm, and more preferably 20 to 30 nm.

The cell-containing device or the cell-embedding device may have, for example, an immunoisolation layer containing a polymer, e.g., the polyvinyl alcohol resin (A). In other words, the cell-containing device may have an immunoisolation layer made of a polymer (a polymer in a gel form) or may have an immunoisolation function exhibited by a polymer (a polymer in a gel form).

The immunoisolation layer or the immunoisolation function refers to a layer or function that prevents permeation of, for example, immune-related proteins, such as antibodies, complements and leucocytes, while allowing permeation of, for example, glucose; hormones such as insulin, thyroid-stimulating hormone, thyroid hormones, parathyroid hormone, growth hormone, thyroxine, glucocorticoids, glucagon, estradiol, and testosterone; proteins such as blood coagulation factors, albumin, globulin, and various enzymes (metabolic enzymes or digestive enzymes such as amylase, protease, and lipase); neurotransmitters, such as dopamine; etc.

The cell-containing device or the cell-embedding device may be, for example, a bioartificial organ etc.

The cell-containing device or the cell-embedding device can be produced by, for example, combining a biological composition and a polymer, and optionally an additional component.

The cell-containing device or the cell-embedding device can be produced by a conventional method selected as appropriate for the types, forms, configurations, etc. of the components.

For example, a liquid mixture containing a polymer and optionally an additional component is preferably formed into a gel.

When the polymer is formed into a gel, the gel may be shaped or formed into a desired shape by, for example, a method involving pouring a liquid mixture (in particular, an aqueous solution that may be in a sol state) containing a polymer, e.g., a polyvinyl alcohol resin and optionally a biological composition, a crosslinking agent and a cell culture component as needed, into a mold of the desired shape to form a gel; or a method involving cutting a produced gel with a knife etc. into the desired shape.

A liquid mixture (in particular, an aqueous solution) containing a polymer, e.g., the polyvinyl alcohol resin and optionally a biological composition, a crosslinking agent and a cell culture component as needed typically undergoes a sol state to become a gel. Such a sol is understood to be an equivalent of the gel according to the present invention and is within the scope of the present invention.

The solid content of the liquid mixture (in particular, an aqueous solution that may be in a sol state) is, for example, 0.3 to 20% by mass, preferably 0.5 to 10% by mass, and more preferably 1 to 8% by mass. A gel prepared from the liquid mixture with such a solid content is preferred because the gel is capable of maintaining the shape of the cell-embedding device implanted in the body for a long period of time and retaining an adhesion preventive ability and has other advantages.

The liquid mixture may be prepared by mixing all the components together. Alternatively, a liquid mixture containing a polymer and optionally a crosslinking agent and a cell culture component as needed (e.g., an aqueous solution of a polyvinyl alcohol resin) may be first prepared, and a biological composition may be added to the mixture.

Other components may be added together with or separately from the biological composition and/or the cell culture component.

The aqueous solution containing a polyvinyl alcohol resin may be prepared in any manner, and may be prepared by a conventionally known method for dissolving a PVA, involving, e.g., dispersing a polyvinyl alcohol resin in water at room temperature, agitating the dispersion while raising the temperature to 80° C. or more to allow complete dissolution, and cooling the solution.

The crosslinking agent may be in the form of an aqueous solution. The aqueous solution of the crosslinking agent may be prepared in any manner, and may be prepared by, e.g., a method involving dispersing the crosslinking agent in water at room temperature, and agitating the dispersion at room temperature to allow dissolution. Alternatively, the aqueous solution of the crosslinking agent may be prepared by a method involving dispersing the crosslinking agent in water at room temperature, agitating the dispersion under heating (e.g., at 60° C. for 10 minutes) to allow dissolution, and leaving the solution to stand at room temperature.

The aqueous solution of the polyvinyl alcohol resin and the aqueous solution of the crosslinking agent are desirably sterilized by a conventionally known method, such as autoclaving, UV, γ-rays or filtering. The addition of a biological composition under mixing and the subsequent production process of the cell-containing device are desirably performed under germ-free conditions. The mixture and the cell-containing device are desirably stored under germ-free conditions.

The aqueous solution of the polyvinyl alcohol resin and the mixture or aqueous solution containing the polyvinyl alcohol resin and the crosslinking agent and optionally a biological composition and/or a cell culture component as needed used in the preparation of the cell-embedding device may be left to stand for a certain period of time.

The temperature at which the mixture or the aqueous solution is allowed to stand may be a temperature suitable for storage of the biological composition.

The duration during which the mixture or the aqueous solution is allowed to stand to prepare a gel (time for gelation or gelation time) may be selected as appropriate for the concentration of the polymer (the polyvinyl alcohol resin etc.), the amount of the crosslinking agent, the temperature at which the mixture or the aqueous solution is allowed to stand, or other factors, but is usually about 1 hour to about one week at normal temperature. The duration during which the mixture or the aqueous solution is allowed to stand is preferably one hour or more so that the cell-embedding device does not easily break when placed in the body.

When a modified PVA resin is used for the preparation of the cell-embedding device, a pH buffer solution or the like may be added to a liquid mixture containing a modified PVA resin and a crosslinking agent and optionally MSCs and/or a cell culture component as needed to adjust the pH of the liquid mixture and control the gelation time. When the pH of the system is lowered, the gelation time tends to be shortened. When the pH of the system is raised, the gelation time tends to be extended.

An example of a production process of the cell-containing or cell-embedding device using a supporting substrate will be described below.

A liquid polymer mixture (e.g., an aqueous solution or an aqueous gel containing a polyvinyl alcohol resin) containing a cell culture component, optionally in a gel form, is placed on a base material or a base plate (e.g., a glass slide). A supporting substrate, such as a PET mesh (e.g., trade name: PET mesh sheet (TN120), Sanplatec Corp.) is stacked on the polymer mixture. A mixture or solution or dispersion or suspension containing a biological composition dissolved or dispersed or suspended in a liquid polymer mixture (e.g., an aqueous solution or an aqueous gel containing a polyvinyl alcohol resin), optionally in a gel form, is spread over the supporting substrate using a gel loading tip etc. Another supporting substrate (e.g., a PET mesh) is stacked on the polymer mixture-loaded PET mesh in such a manner that the polymer mixture is sandwiched between the supporting substrates. A liquid polymer mixture (e.g., an aqueous solution or an aqueous gel containing a polyvinyl alcohol resin) containing a cell culture component, optionally in a gel form, is placed on the supporting substrate (e.g., a PET mesh). Another base material or base plate (e.g., a glass slide) is stacked on the supporting substrate. The base materials or the base plates (e.g., glass slides) are removed from the assembled polymer mixture and the supporting substrates to give a cell-containing device according to an aspect of the present invention.

The present invention also includes an implantation method, in particular, a method for implanting the cell-containing device, as described above. In the implantation method, the cell-containing device is implanted into the site from which the device 1 has been implanted and subsequently at least the non-bioabsorbable material has been retrieved as described above. According to such an implanting method, various diseases or symptoms can be prevented or improved depending on the biological composition (cells or tissue) used. The present invention thus also includes a method for preventing and/or treating or improving a disease or a symptom.

Such a method includes implanting the cell-containing device after the device 1 has been implanted and subsequently at least the non-bioabsorbable material has been retrieved, and may, of course, include implanting or placing the device 1 before the implantation of the cell-containing device.

Examples of the disease or symptom include, for example, endocrine diseases, such as thyroid diseases, parathyroid diseases, adrenal diseases, pituitary diseases, and pineal diseases; metabolic diseases, such as ornithine transcarbamylase deficiency, hyperammonemia, hypercholesterolemia, homocystinuria, glycogenosis, Crigler-Najjar syndrome, and Wilson's disease; diabetes mellitus, such as type 1 diabetes mellitus, type 2 diabetes mellitus, and pancreatic diabetes; neurodegenerative diseases, such as Parkinson's disease, Alzheimer's disease, amyotrophic lateral sclerosis, and spinocerebellar degeneration; hemophilia; bone diseases such as osteoporosis; cancers such as leukemia; etc.

The duration of the implantation or placement of the cell-containing device may be, for example, but is not limited to, 10 days or more, one month or more, two months or more, three months or more, six months or more, one year or more, etc.

The device 1 of the present invention is suitable for used in combination with the cell-containing device as described above. The present invention thus includes a combination device (or a kit, a device or a combination) comprising the device 1 and the cell-containing device.

EXAMPLES

The present invention will be described in more detail with reference to Examples, but is not limited thereto.

Various modifications may be made by a person having ordinary skill in the art, without departing from the technical idea of the present invention.

Compressive Deformation of Non-Woven Fabric

A cylinder shape with a diameter of 4 mm was punched out from a non-woven fabric produced by the method as described later, and left to be immersed in purified water at 37° C. overnight. A physical property testing system, a creep meter RE2-33005C (Yamaden Co., Ltd.) was used to measure the thickness (H1) of the non-woven fabric, and then the non-woven fabric was compressed with a plunger of 40 mm in diameter at a rate of 0.05 mm/sec. The compressive elastic modulus (kPa) at a strain of 1 to 5%, and the intermediate compressive stress (kPa) at a strain of 10%, 20% and 30% were measured. The percentage of change in thickness (the percentage of strain) when compressed with a stress of 1 kPa was calculated relative to the thickness under no load conditions (0% strain), and taken as a percentage of compressive deformation.

Visible Light Transmittance of Non-Woven Fabric

A non-woven fabric sample (1.0 mm in thickness) was left to be immersed in purified water in the same manner as above. Transmittance of light at a wavelength from 400 to 800 nm through the swollen fabric sample was measured using SYNERGY H1 (BioTek) at intervals of 10 nm. Average transmittance of light at a wavelength from 400 to 800 nm was calculated and taken as a visible light transmittance.

Diameter of Fibers Constituting Non-Woven Fabric and its Variation in the Longitudinal Direction Images of a non-woven fabric were taken with a scanning electron microscope (SEM, Hitachi High-Technologies Corporation, FlexSEM 1000, at a magnification of 100-fold and 500-fold). From the images, 50 fibers were randomly selected to measure the mean fiber diameter and its variation in the longitudinal direction.

Water Content of Non-Woven Fabric

The dry mass (Ws) of a non-woven fabric produced by the method as described later was measured. The non-woven fabric was immersed in distilled water at 37° C. for 24 hours to allow the fabric to sufficiently swell. The non-woven fabric was taken out of the distilled water, and the excessive moisture between the fibers was removed with dry paper towels. The wet mass (Wh) of the non-woven fabric was measured. The mass of water (Ww) was determined from Ws and Wh, and the water content (%) of the non-woven fabric was calculated by the equation below. The average water content of three samples is indicated herein.

$$\text{Water content } (\%) = Ww/(Ws+Ww) \times 100 = (Wh-Ws)/(Wh) \times 100$$

Ww: mass of water(wet mass−dry mass)
Ws: solid mass(dry mass)

Analysis of Modified PVA Resins

The viscosity of a 4% aqueous solution of a modified PVA resin and the degree of saponification of a modified PVA resin were determined in accordance with JIS K 6726 (1994).

The amount of diacetone acrylamide units, i.e., the degree of modification was determined from the integral value of the peaks attributed to the units in $^1$H-NMR analysis using DMSO-$d_6$ as the solvent.

Analysis of Crosslinking Agent (Polyacrylic Acid Hydrazide)

The weight average molecular weight of a crosslinking agent was determined by size exclusion chromatography under the following conditions.

Measurement Conditions:

Solvent: a 50 mM aqueous solution of sodium dihydrogen phosphate

Polymer concentration: 1 mg/mL

Flow rate: 1.0 mL/min

Column temperature: 40° C.

Column: Shodex OHPak SB-803HQ, Shodex OHPak SB-805HQ

Standard: pullulan

Detector: RI

The degree of hydrazidation was determined by back titration of 12 using a sodium thiosulfate standard solution. The details of the experimental procedures are as follows.

Experimental Procedures:

1. An $I_2$/MeOH solution was prepared.

2. The $I_2$/MeOH solution was titrated using a 0.1 M sodium thiosulfate standard solution (the concentration was determined to be 0.047 M in this measurement).

3. A polymer sample was precisely weighed and dissolved in 20 mL of ion exchanged water.

4. The 0.047 M $I_2$/MeOH solution was added to 2.0 mL of the solution prepared in step 3.

5. Back titration of $I_2$ was performed using the 0.1 M sodium thiosulfate standard solution.

Evaluation of Device

The device of the invention (the implantation device or the device 1) was implanted or placed into a subcutaneous site in rats or mice and formation of an encapsulating membrane was induced. The device was retrieved, and a pancreatic islet-containing device was then implanted into the subcutaneous site. The device of the invention was evaluated through the evaluation of the functions of the pancreatic islet-containing device.

In particular, a pancreatic islet-containing device was implanted into streptozotocin-induced diabetic rats, and the blood glucose levels were measured over time to evaluate the therapeutic effect of the device on diabetes mellitus.

Glucose Tolerance Test (IPGTT)

Glucose tolerance test was performed days 43 to 47 after the pancreatic islet-containing device was implanted. Mice were fasted for 14 hours. D-glucose (1.0 g/kg) was intraperitoneally injected to the mice. Blood glucose levels were measured before the injection and 5, 10, 15, 20, 25, 30, 45, 60, 90 and 120 minutes after the injection. Blood glucose response curves were generated and the areas under the curve (AUCs) were determined for comparison.

Computerized Tomography (CT) Angiography

CT angiography was performed week six after the device of the invention (the implantation device or the device 1) was implanted. Prior to CT imaging, 4 μL/g body weight of ExiTron nano 12000 (Miltenyi Biotec) was intravenously injected via the tail vein. ExiTron nano 12000 is a high density, alkaline earth metal-based nanoparticulate contrast agent specifically formulated for CT of animals. The average diameter of the nanoparticles is 110 nm, which is the detection threshold for newly formed blood vessels. CT angiography was performed using an X-ray CT scanner for experimental animals (Latheta LCT-200; Hitachi). The blood vessel volume was calculated in the encapsulating membrane tissue around the non-bioabsorbable material. To extract capillary blood vessels, the CT number for analyzing the vascular region was defined as 100 or more.

Immunohistochemical Assay

Immunohistochemical assay was performed day 7 after the pancreatic islet-containing device was implanted. For immunohistochemical staining, tissue around the implantation site was harvested and fixed in 4% paraformaldehyde and embedded in paraffin. The specimens were immunohistochemically stained with anti-von Willebrand factor (vWF) (ab7356; Merck Millipore), anti-collagen III (ab7778; Abcam), anti-collagen IV (ab6586; Abcam) and anti-laminin (ab11575; Abcam) antibodies. EnVision+ System HRP-conjugated polymer rabbit antibody (4003; DAKO) was used as a secondary antibody. For examination of angiogenesis, vWF-positive cells were counted in the pancreatic islets and the stromal region. Collagen III-, collagen IV- or laminin-positive cells were defined as significant immunopositive cells detectable in the encapsulating membrane tissue around the pancreatic islets.

Real-Time PCR

At week six after the device of the invention (the implantation device or the device 1) was implanted, RNA was extracted from the encapsulating membrane tissue surrounding the non-bioabsorbable material. Relative gene expression was determined using TaqMan Array 96-well FAST plates (4413257; Applied Biosystems). TaqMan Array contained 46 target genes and 2 endogenous control gene candidates. Samples were analyzed using StepOnePlus Real-Time polymerase chain reaction (PCR) system (Applied Biosystems) under amplification conditions of 50° C. for 2 min, 95° C. for 20 sec, followed by 40 cycles of 95° C. for 1 sec and 60° C. for 20 sec. The results were analyzed by Expression Suite Software ver. 1.3 (Applied Biosystems). Relative quantification (RQ) was calculated by the comparative CT method. A group that did not receive the non-woven fabric was used as a calibrator to determine the relative gene expression of device-implantation groups. 18S was used as a housekeeping gene.

Statistical Analysis

All the data are expressed as the mean±SD. All the statistical analyses were performed using a JMP Pro 15 software program (SAS Institute Inc.). Changes in IPGTT were analyzed by two-way analysis of variance (ANOVA), and post hoc comparisons among groups were performed by the Tukey-Kramer test. AUCs of IPGTT were analyzed by the Kruskal-Wallis test followed by the Dunn's post hoc test. The number of vWF-positive blood vessels was analyzed by one-way ANOVA and the Mann-Whitney U test. The percentage of immunopositivity of ECM staining was analyzed by the Pearson's chi-square test, and post hoc comparisons among groups were performed by the Fisher's exact test. Kaplan-Meier curves were compared by the log-rank test. A p value of <0.05 was considered statistically significant.

Example 1

Production of Non-Woven Fabric

A gelatin was purchased from Nitta Gelatin, Inc. (jelly strength: 262 g, ingredient: alkaline treated bovine bone) and dissolved in water at 60° C. at a mass ratio of gelatin: water=3:5 (gelatin concentration: 37.5% by mass). The viscosity of the gelatin solution at 60° C. was 960 to 970 mPa·s. The aqueous gelatin solution was used as a spinning solution to produce a non-woven fabric (a filament non-woven fabric) using the production device for a non-woven fabric as shown in FIG. 4 in WO 2018-235745. The production of the non-woven fabric was performed using the spinning solution at 60° C. and discharge nozzles of 250 μm in diameter (inner diameter) and 5 mm in height with a discharge pressure of 0.2 MPa under conditions of an air pressure of 0.375 MPa and an air temperature of 100° C. The distance between the fluid ejection holes and the discharge nozzles was set at 5 mm, and the collection distance was set at 50 cm. The produced non-woven fabric was wound up with a winding roller.

The non-woven fabric was air-dried at a normal temperature overnight, and subjected to thermal dehydration crosslinking. The crosslinking was performed at 140° C. for 48 hours.

A 22-mm diameter cylinder with a thickness of 0.5 mm was punched out from the non-woven fabric to produce a non-woven fabric 1.

The non-woven fabric 1 was left to be immersed in purified water at 37° C. overnight. The non-woven fabric 1 after being left to be immersed in purified water had a compressive deformation of 15.1%, a visible light transmittance of 21.7%, and a mean fiber diameter of 49.6 μm. The fiber diameter varied from 32.1 to 73.3 μm. The non-woven fabric 1 was examined under an inverted microscope (CKX53, Olympus, at a magnification of 4-fold) equipped with a digital microscope (AxioCAM ERc5, Zeiss), and the fibers in the non-woven fabric were observed to be at least partially fusion bonded at intersections of the fibers. The water content of the non-woven fabric 1 after being left to be immersed in purified water was 79.3%.

Production of Non-Bioabsorbable Material

A 26-mm diameter cylinder with a thickness of 0.5 mm was punched out from a commercially available silicone rubber (Cat. No. 6-611-02, thickness: 1 mm, AS ONE Corporation) and used as a non-bioabsorbable material 2.

Production of Device

Two pieces of the non-woven fabric 1 were left to be immersed in physiological saline at 22° C. for 1 minute to allow the fabric to sufficiently swell.

Each of the two pieces of the non-woven fabric 1 swollen with saline was mounted on either of the front and back sides of the non-bioabsorbable material 2, and fixed on the non-bioabsorbable material 2 by suturing with a suture to produce a device of the invention (an implantation device or device 1).

Implantation and Placement of Device

The device of the invention (the implantation device or the device 1) was subcutaneously placed in 12- to 14-week-old male Wistar rats (Japan SLC) for six weeks. There was no bleeding or release of exudates in the subcutaneous site prior to the placement of the device, and an encapsulating membrane was not observed. After placing the device for six weeks, sufficient formation of an encapsulating membrane in the subcutaneous site was observed even with the naked eye, as compared with before the placement of the device.

The non-woven fabric 1 of the device was nearly completely absorbed by the body and the surrounding tissue and formed an encapsulating membrane, and only the non-bioabsorbable material remained at the placement site (implantation site). There were few adhesions between the surface of the non-bioabsorbable material and the subcutaneous site, and the non-bioabsorbable material was easily separated from the subcutaneous tissue. After the non-bioabsorbable material was retrieved, no bleeding or release of exudates at all was observed in the subcutaneous site from which the non-bioabsorbable material was retrieved.

Due to these, after retrieval of the device, implantation of another cell, tissue or device was easily carried out on the site. For example, the pancreatic islet-embedding device as described later was easily inserted into the site.

The implantation or placement of the device 1 was performed on four rats, and the rats showed similar results, i.e., the rats showed formation of a sufficient amount of an encapsulating membrane and no bleeding or release of exudates when the device 1 was retrieved.

Preparation of Pancreatic Islet Cells for Pancreatic Islet-Embedding Device

Pancreatic islets were isolated from 11- to 14-week-old male Lewis rats (Japan SLC). Cold Hanks' balanced salt solution (HBSS) containing 0.8 mg/mL collagenase type V (Sigma-Aldrich) was injected through the common bile duct into the pancreas of the rats to digest the pancreas at 37° C. for 12 minutes to separate pancreatic islets from the pancreatic tissue. Concentration gradient centrifugation was performed using Histopaque-1119 (Sigma-Aldrich) and Lymphoprep (Axis-Shield, Norway) to collect the pancreatic islets. The pancreatic islets were cultured in RPMI 1640 medium containing 5.5 mmol/L glucose and 10% fetal bovine serum (FBS) under 5% $CO_2$ at 37° C. overnight.

Synthesis of Polymer for Pancreatic Islet-Embedding Device

Into a flask equipped with an agitator, a thermometer and a dropping-funnel with a reflux condenser were placed 2,000 parts of vinyl acetate, 143 parts of methanol and 3.7 parts of di acetone acrylamide. The air in the system was replaced with nitrogen, and the internal temperature was raised to 60° C. A solution of 0.16 parts of 2,2-azobis(isobutyronitrile) in 100 parts of methanol was added to initiate polymerization. Immediately after the initiation of polymerization, a solution of 70.1 parts of diacetone acrylamide in 46.7 parts of methanol was added dropwise at a constant rate while allowing nitrogen to flow through the flask. At 210 minutes after the initiation of polymerization, m-dinitrobenzene was added as a polymerization terminator to stop the polymerization. The yield at the end of polymerization was 47.1%. Methanol vapor was added to the resulting reaction mixture to distill off the remaining vinyl acetate to give a 35% solution of a diacetone acrylamide-vinyl acetate copolymer in methanol. To 500 parts of this solution, 70 parts of methanol, 1 part of ion exchanged water and 29.3 parts of a 4% solution of sodium hydroxide in methanol were added, and the mixture was thoroughly agitated at 45° C. to allow a saponification reaction to proceed. The resulting gelatinous material was pulverized, washed thoroughly with methanol and dried to give D-PVA 1. A 4% aqueous solution of D-PVA 1 had a viscosity of 53.4 mPa·s. D-PVA 1 had a degree of saponification of 98.4 mol % and contained 3.6 mol % diacetone acrylamide units.

Synthesis of Crosslinking Agent for Pancreatic Islet-Embedding Device

To an aqueous solution of 20 parts of polyacrylamide with a weight average molecular weight of about 40,000 in 40 parts of ion exchanged water was added 16 parts of hydrazine monohydrate, and the mixture was reacted at 80° C. for 15 hours. Ethanol was added to the liquid mixture, and the precipitate was filtered, washed and dried to give APA 1. APA 1 had a weight average molecular weight of about 53,000 and a degree of hydrazidation of 88%.

Preparation of Aqueous Solution of Modified PVA Resin and Crosslinking Agent in a Sol State To a 25 mL tube were added 8.0 g of a 6.25% aqueous solution of D-PVA 1 prepared in Synthetic Example 1 and 1.0 mL of 10×HBSS (Hanks' balanced salt solution), and the mixture was agitated by shaking the tube up and down.

The mixture was spin down in a centrifuge (trade name: Hybrid high-speed refrigerated centrifuge 6200, Kubota Corporation), and the mixture was left to stand at 37° C. for 10 minutes. Then, 1.0 mL of a 5% aqueous solution of APA 1 prepared in Synthetic Example 9 was added as a crosslinking agent, and the tube was shaken up and down 15 times. The mixture was spin down in the centrifuge, and the tube was again shaken up and down 15 times.

The mixture was centrifuged at 3,000 rpm at 25° C. for 1 minute and left to stand at 37° C. The viscosity of the aqueous solution in a sol state was checked at appropriate intervals until the sol beaded up within 3 to 4 seconds, indicating that the sol was in a state optimal for embedding pancreatic islets. The tube was taken out of the hot bath, and left to stand on ice for 1 minute. The tube was centrifuged at 3,000 rpm at 25° C. for 1 minute to give a sol containing the modified PVA resin in an amount of 5% and the crosslinking agent in an amount of 0.5%.

The concentration of D-PVA 1 in the gel (hydrogel) was 5.0%, and the concentration of APA 1 in the gel was 0.5%. The stress sustained by the gel prepared in accordance with the formulation was 5.2 kPa.

Preparation of Pancreatic Islet-Embedding Device

An amount of 160 µL of the sol prepared on a dish was placed on a glass slide. A PET mesh (trade name: PET mesh sheet (TN120), Sanplatec Corp.) was placed on the sol. The culture medium components were removed from the prepared pancreatic islet cells as thoroughly as possible, and the cells were suspended in 50 µL of an aliquot of the sol to prepare a suspension. The suspension of the pancreatic islet cells was spread over the PET mesh. Another PET mesh was further stacked on the sol-loaded PET mesh in such a manner that the suspension of the pancreatic islet cells (18,000 Islet Equivalents (IEQ): IEQ is an international unit of the number of pancreatic islets; one IEQ is defined as a single islet of 150 µm in diameter) was sandwiched between the PET meshes. On the PET meshes, 140 µL of the sol was placed. Another glass slide was then mounted on the sol. The assembled sol and PET meshes were placed in a moist chamber, and left to stand at 4° C. for 48 hours to prepare a pancreatic islet-embedding device (in the form of an aqueous gel).

Storing of Pancreatic Islet-Embedding Device

The pancreatic islet-embedding device assembled as above was taken off the glass slides, immersed in 5 mL/well of a preservation medium (RPMI 1640 medium containing 10% FBS and glucose adjusted to a concentration of 5.5 mM) in a 6-well plate, and stored at 4° C. for about 16 hours.

Implantation Step

The device 1 was placed in rats, and about five weeks after the placement of the device 1 (about one week prior to implantation of the pancreatic islet-embedding device), streptozotocin was injected to induce diabetes mellitus.

At six weeks after the placement of the device 1, the non-bioabsorbable material 2 was retrieved. The pancreatic islet-embedding device (in the form of an aqueous gel) after storage was implanted by placing it into the subcutaneous site in the rats, i.e., the implantation site of the device 1 or the subcutaneous site from which the non-bioabsorbable material 2 was retrieved.

At the time of the implantation of the pancreatic islet-embedding device, an encapsulating membrane, i.e., an encapsulating membrane containing the non-woven fabric 1 or the gelatin, was retained.

Evaluation of Therapeutic Effect on Diabetes Mellitus

After implantation of the pancreatic islet-embedding device, the blood glucose levels were measured over time to evaluate the therapeutic effect.

The evaluation of the therapeutic effect on diabetes mellitus was performed on four rats.

Comparative Example 1

The evaluation of the therapeutic effect on diabetes mellitus was performed in the same manner as in Example 1 except that the implantation or placement of the device 1 was not performed.

The evaluation of the therapeutic effect on diabetes mellitus was performed on four rats.

Reference Example 1

The implantation and the evaluation of the therapeutic effect on diabetes mellitus were performed in the same manner as in Example 1 except that a commercially available gelatin sponge (Gelfoam, Pfizer, Inc.) was used in place of the non-woven fabric 1.

The therapeutic effect on diabetes mellitus was not observed in two rats, and no further experiments were performed using other rats.

Reference Example 2

A commercially available gelatin (RM-50, Jellice Co., Ltd.) was used in place of the non-woven fabric 1, but the gelatin was dissolved in physiological saline, and the device was not able to be produced.

The results of the evaluation of the therapeutic effect on diabetes mellitus in Example 1 and Reference Examples 1 and 2 are summarized in Table 1 below.

The blood glucose levels before implantation refer to the blood glucose levels measured just before the pancreatic islet device was implanted after the retrieval of the device 1.

TABLE 1

| | | | Pancreatic islet device | | |
|---|---|---|---|---|---|
| | Form of gelatin in implantation device | Rat No. | Blood glucose levels before implantation (mg/dL) | Blood glucose levels 30 days after implantation (mg/dL) | Blood glucose levels 60 days after implantation (mg/dL) |
| Example 1 | Non-woven fabric 1 | 1 | 478 | 51 | 50 |
| | | 2 | 460 | 53 | 84 |
| | | 3 | 488 | 57 | 78 |
| | | 4 | 501 or more | 73 | 112 |
| Comparative Example 1 | None | 1 | 407 | 485 | 402 |
| | | 2 | 409 | 306 | 375 |
| | | 3 | 497 | 370 | 369 |
| | | 4 | 460 | 315 | 340 |
| Reference Example 1 | Sponge | 1 | 452 | 443 | 468 |
| | | 2 | 440 | 439 | 443 |

As apparent from the results shown in the table above, the implantation device of Example 1 formed an encapsulating membrane that was derived from the non-woven fabric, i.e., the gelatin-containing non-woven fabric, and activated the subcutaneous implantation site, thereby allowing the subsequently implanted pancreatic islet device to effectively perform its functions.

Such an ability of the device of Example 1 to allow the pancreatic islet device to effectively exhibit its functions was unexpected since the device of Example 1 was free of growth factors or other factors.

The device of Example 1 induced such activation and caused no bleeding or release of exudates in the implantation site when the device was retrieved. In this manner, the device of Example 1 facilitated efficient implantation of another device and allowed the implanted device to efficiently exhibit or achieve its functions.

Example 2

Production, Implantation and Placement of Device

A 11-mm diameter cylinder with a thickness of 0.5 mm was punched out from a non-woven fabric prepared in the same manner as in Example 1 to produce a non-woven fabric 3.

The non-woven fabric 3 was left to be immersed in purified water at 37° C. overnight. The non-woven fabric 3 after being left to be immersed in purified water had a compressive deformation of 15.1%, a visible light transmittance of 21.7%, and a mean fiber diameter of 49.6 μm. The fiber diameter varied from 32.1 to 73.3 μm. The non-woven fabric 3 was examined under an inverted microscope (CKX53, Olympus) equipped with a digital microscope (AxioCAM ERc5, Zeiss, at a magnification of 4-fold), and the fibers in the non-woven fabric were observed to be at least partially fusion bonded at intersections of the fibers.

A 11-mm diameter cylinder with a thickness of 0.5 mm was punched out from a commercially available silicone rubber (Cat. No. 6-611-01, thickness: 0.5 mm, AS ONE Corporation) and used as a non-bioabsorbable material 4.

A device (an implantation device or a device 1) was then produced in the same manner as in Example 1.

The device (the implantation device or the device 1) was placed into a subcutaneous site in mice for six weeks. There was no bleeding or release of exudates in the subcutaneous site prior to the placement of the device, and an encapsulating membrane was not observed. After placing the device for six weeks, sufficient formation of an encapsulating membrane in the subcutaneous site was observed even with the naked eye, as compared with before the placement of the device.

The non-woven fabric 3 of the device was nearly completely absorbed by the body and the surrounding tissue and formed an encapsulating membrane, and only the non-bioabsorbable material remained at the placement site (implantation site). There were few adhesions between the surface of the non-bioabsorbable material and the subcutaneous site, and the non-bioabsorbable material was easily peeled off After the non-bioabsorbable material was retrieved, no bleeding or release of exudates at all was observed in the subcutaneous site from which the non-bioabsorbable material was retrieved.

Due to these, after retrieval of the device, implantation of another cell, tissue or device was easily carried out on the site. For example, the pancreatic islet cells as described later were easily inserted into the site.

The implantation or placement of the device 1 was performed on four mice, and the mice showed similar results, i.e., the rats showed formation of a sufficient amount of an encapsulating membrane and no bleeding or release of exudates when the device 1 was retrieved.

Preparation of Pancreatic Islet Cells Pancreatic islets were isolated from 8- to 14-week-old male C57BL/6 mice (Japan SLC). Cold Hanks' balanced salt solution (HB SS) containing 1 mg/mL collagenase type V (Sigma-Aldrich) was injected through the common bile duct into the pancreas of the mice to digest the pancreas at 37° C. for 12 minutes to separate pancreatic islets from the pancreatic tissue. Concentration gradient centrifugation was performed using His-topaque-1119 (Sigma-Aldrich) and Lymphoprep (Axis-Shield, Norway) to collect the pancreatic islets. The pancreatic islets were cultured in RPMI 1640 medium containing 5.5 mmol/L glucose and 10% fetal bovine serum (FBS) under 5% $CO_2$ at 37° C. overnight.

Implantation Step

The device 1 was placed in mice, and about five weeks after the placement of the device 1 (about one week prior to implantation of pancreatic islet cells), streptozotocin was injected to induce diabetes mellitus.

At six weeks after the placement of the device 1, the non-bioabsorbable material 4 was retrieved. The pancreatic islet cells (400 IEQs) prepared above were implanted as a cell-containing device by placing the cells into the subcutaneous site in the mice, i.e., the implantation site of the device 1 or the subcutaneous site from which the non-bioabsorbable material 4 was retrieved. The therapeutic effect on diabetes mellitus was then evaluated.

The evaluation of the therapeutic effect on diabetes mellitus was performed on four mice.

At the time of the implantation of the pancreatic islet cells, an encapsulating membrane, i.e., an encapsulating membrane containing the non-woven fabric 3 or the gelatin, was retained.

Comparative Example 2

The evaluation of the therapeutic effect on diabetes mellitus was performed in the same manner as in Example 2 except that the implantation or placement of the device 1 was not performed.

The evaluation of the therapeutic effect on diabetes mellitus was performed on four mice.

The results of the evaluation of the therapeutic effect on diabetes mellitus in Example 2 and Comparative Example 2 are summarized in Table 2 below.

TABLE 2

| | | | Pancreatic islet cells | |
| | Form of gelatin in implantation device | Mouse No. | Blood glucose levels before implantation (mg/dL) | Blood glucose levels 40 days after implantation (mg/dL) |
| --- | --- | --- | --- | --- |
| Example 2 | Non-woven fabric 3 | 1 | 501 or more | 123 |
| | | 2 | 501 or more | 179 |
| | | 3 | 501 or more | 183 |
| | | 4 | 501 or more | 140 |
| Comparative Example 2 | None | 1 | 473 | 501 or more |
| | | 2 | 501 or more | 281 |
| | | 3 | 501 or more | 501 or more |
| | | 4 | 501 or more | 501 or more |

As apparent from the results shown in the table above, even when the device of Example 2 was used in place of the device of Example 1, and mice were used in place of rats, and pancreatic islet cells were used in place of the pancreatic islet-containing device, a tendency similar to that in Example 1 was observed, and the device allowed the pancreatic islet cells to effectively perform its functions.

Example 3

The implantation device of Example 2 was further evaluated by intraperitoneal glucose tolerance test (IPGTT), computerized tomography (CT) angiography, immunohistochemical assay and real-time PCR. IPGTT, CT angiography, immunohistochemical assay and real-time PCR were performed on 15, 4, 5 and 8 mice, respectively. The results were expressed by the mean values.

The AUC of IPGTT in the intraperitoneal glucose tolerance test was reduced by 15,923 min·mg/dL as compared with that in mice without the implantation of the non-woven fabric 3. These results were consistent with the results shown in the Table 2 above.

The blood vessel volume as determined by CT angiography was increased by 8.8 mm$^3$ as compared with that in mice without the implantation of the non-woven fabric 3. The immunohistochemical assay was assessed by the calculation as shown in the table below. In this calculation, X1 represents immunopositivity (%) when the non-woven fabric 3 was not used, X2 represents immunopositivity (%) when the implantation device of Example 2 was used, Y1 represents the number of vWF-positive blood vessels per mm$^2$ when the non-woven fabric 3 was not used, and Y2 represents the number of vWF-positive blood vessels per mm$^2$ when the implantation device of Example 2 was used.

TABLE 3

| | | X2 − X1 (%) | Y2 − Y1 (blood vessels/mm$^2$) |
|---|---|---|---|
| Surrounding region of pancreatic islets | Collagen III | 17.2 | — |
| | Collagen IV | 27.0 | — |
| | Laminin | 25.8 | — |
| | Number of vWF-positive newly formed blood vessels | — | −20.3 |
| Stromal region | Number of vWF-positive newly formed blood vessels | — | 156.5 |

The results of the experiments further confirmed that the device of Example 2 allows the subsequently implanted pancreatic islets to efficiently exhibit its functions. The blood vessel volume was moderately increased even without using a growth factor, and increase of the extracellular matrix in the encapsulating membrane was also observed.

The genes that showed statistical significance in real-time PCR are shown in the table below. As shown in the table below, the device of Example 2 increased the levels of IGF-2 and other factors in the encapsulating membrane.

TABLE 4

| Target gene | log2 relative quantification | P value |
|---|---|---|
| IGF-2 | 5.939 | p < 0.01 |
| EGF | 1.818 | |
| FGF-12 | 1.932 | p < 0.05 |
| IGF-1 | 2.144 | |

TABLE 4-continued

| Target gene | log2 relative quantification | P value |
|---|---|---|
| HGF | 2.615 | |
| TGF-β1 | 2.421 | |
| Collagen III | 2.275 | |
| N-cadherin | 2.499 | |
| c-MET | 1.925 | |
| VCAM-1 | 2.789 | |
| HIF-1a | 1.731 | |
| Vasohibin-1 | 1.949 | |
| Collagen IV | 1.544 | |
| PDGF-A | 1.719 | |
| TSP-2 | 2.448 | |
| ICAM-1 | 2.326 | |
| CD31 | 2.198 | |
| Versican | 1.538 | |
| PDGF-B | 1.155 | |

Example 4

The evaluation of the therapeutic effect on diabetes mellitus was performed in the same manner as in Example 1 except that the amount of the pancreatic islet cells that were embedded in the pancreatic islet device was reduced to 10,500 IEQs.

Example 5

A non-woven fabric 4 was produced in the same manner as in Example 1 except that thermal dehydration crosslinking was performed at 155° C. for 24 hours. The non-woven fabric 4 after being left to be immersed in purified water had a compressive deformation of 17.6%, a visible light transmittance of 29.0%, and a mean fiber diameter of 38.5 μm. The fiber diameter varied from 26.2 to 67.3 μm. The fibers in the non-woven fabric were observed to be at least partially fusion bonded at intersections of the fibers, as with the non-woven fabric 1. The water content of the non-woven fabric 4 was 74.6%, indicating that the degree of thermal crosslinking was greater than that in the non-woven fabric 1.

The evaluation of the therapeutic effect on diabetes mellitus was performed in the same manner as in Example 1 except that the non-woven fabric 4 was used in place of the non-woven fabric 1 and that the amount of the pancreatic islet cells that were embedded in the pancreatic islet device was reduced to 10,500 IEQs.

At the time of the implantation of the pancreatic islet device, the encapsulating membrane, i.e., the encapsulating membrane containing the non-woven fabric 4 or the gelatin, was retained.

Comparative Example 3

The evaluation of the therapeutic effect on diabetes mellitus was performed in the same manner as in Example 1 except that the device 1 was not implanted or placed and that the amount of the pancreatic islet cells that were embedded in the pancreatic islet device was reduced to 10,500 IEQs.

The results of the evaluation of the therapeutic effect on diabetes mellitus in Examples 4 and 5 and Comparative Example 3 are summarized in Table 5 below.

TABLE 5

| | Form of gelatin in implantation device | Rat No. | Pancreatic islet device | |
| | | | Blood glucose levels before implantation (mg/dL) | Blood glucose levels 21 days after implantation (mg/dL) |
| --- | --- | --- | --- | --- |
| Example 4 | Non-woven fabric 1 | 1 | 466 | 92 |
| | | 2 | 482 | 258 |
| Example 5 | Non-woven fabric 4 | 1 | 501 or more | 76 |
| | | 2 | 501 or more | 106 |
| Comparative Example 3 | None | 1 | 481 | 397 |
| | | 2 | 501 or more | 455 |

As apparent from the results shown in the table above, the devices of Examples 4 and 5 formed an encapsulating membrane that was derived from the non-woven fabric, i.e., the gelatin-containing non-woven fabric, and activated the subcutaneous implantation site even without using a growth factor etc., as with Example 1, thereby allowing the subsequently implanted pancreatic islet device to effectively perform its functions. The implantation device of Example 5 more effectively allowed the pancreatic islet device to exhibit its functions as compared with the implantation device of Example 4 (Example 1).

The implantation devices of Examples 4 and 5 were able to be retrieved without bleeding or release of exudates and facilitated efficient implantation of another device, as with the device of Example 1.

Indus Trial Applicability

The present invention provides a novel gelatin-containing device and others. The device of the invention is applicable as a device for activating an implantation site, for example, a device for restoring an injury, or a device adapted to allow a separately implanted cell-containing device to exhibit its intrinsic, sufficiently high performance.

The invention claimed is:

1. An implantation device comprising a bioabsorbable non-woven fabric containing a gelatin, wherein the non-woven fabric has a compressive deformation of 40% or less as measured when the non-woven fabric in a water-swollen state is compressed with a stress of 1.0 kPa.

2. The device according to claim 1, wherein the non-woven fabric has been subjected to crosslinking.

3. The implantation device of claim 1 wherein the non-woven fabric has a visible light transmittance of 10% or more as measured on the non-woven fabric in a water-swollen state.

4. The device according to claim 1, wherein the non-woven fabric has a water content of 200% by mass or less as measured on the non-woven fabric in the water-swollen state.

5. The implantation device of claim 1 wherein the non-woven fabric has a diameter that varies in a longitudinal direction of the non-woven fabric.

6. The implantation device of claim 1 wherein fibers in the non-woven fabric are partially fusion bonded at intersections of the fibers.

7. The device according to claim 1, wherein the non-woven fabric has a mean fiber diameter (D) of 1 to 70 μm, and wherein the mean fiber diameter varies within a range of $D-0.5D \leq D \leq D+0.5D$.

8. The implantation device of claim 1 wherein the non-woven fabric forms at least part of a surface of the device.

9. The implantation device of claim 1 wherein the device comprises a non-woven fabric and a non-bioabsorbable material.

10. The device according to claim 9, wherein the non-woven fabric is integrated with the non-bioabsorbable material.

11. The device according to claim 9, wherein the non-bioabsorbable material is contained in an amount of 1 part by volume or more relative to 100 parts by volume of the non-woven fabric.

12. The device according to claim 10, wherein the non-bioabsorbable material is contained in an amount of 10 parts by volume or more relative to 100 parts by volume of the non-woven fabric, and wherein the non-woven fabric forms at least part of a surface of the device.

13. The device according to claim 9, wherein the non-bioabsorbable material has an adhesion preventive ability.

14. The device according to claim 1, wherein the device is substantially free of growth factors.

15. A method for implanting the device according to claim 1, comprising implanting the device into an implantation site.

16. The method according to claim 15, wherein the implantation site is a subcutaneous site.

\* \* \* \* \*